(12) United States Patent
Gao et al.

(10) Patent No.: US 11,767,536 B2
(45) Date of Patent: Sep. 26, 2023

(54) METHOD FOR OBTAINING GLYPHOSATE-RESISTANT RICE BY SITE-DIRECTED NUCLEOTIDE SUBSTITUTION

(71) Applicant: Institute of Genetics and Developmental Biology, Chinese Academy of Sciences, Beijing (CN)

(72) Inventors: Caixia Gao, Beijing (CN); Jun Li, Beijing (CN)

(73) Assignee: Institute of Genetics and Developmental Biology, Chinese Academy of Sciences, Beijing (CN)

( * ) Notice: Subject to any disclaimer, the term of this patent is extended or adjusted under 35 U.S.C. 154(b) by 232 days.

(21) Appl. No.: 15/752,514

(22) PCT Filed: Aug. 15, 2016

(86) PCT No.: PCT/CN2016/095307
§ 371 (c)(1),
(2) Date: Feb. 13, 2018

(87) PCT Pub. No.: WO2017/028768
PCT Pub. Date: Feb. 23, 2017

(65) Prior Publication Data
US 2019/0062779 A1 Feb. 28, 2019

(30) Foreign Application Priority Data
Aug. 14, 2015 (CN) .......................... 201510500930.8

(51) Int. Cl.
*C12N 15/82* (2006.01)
*C12N 5/14* (2006.01)
*C12N 15/66* (2006.01)
*C12N 9/10* (2006.01)

(52) U.S. Cl.
CPC ........... *C12N 15/8275* (2013.01); *C12N 5/14* (2013.01); *C12N 9/1092* (2013.01); *C12N 15/66* (2013.01); *C12N 15/8213* (2013.01); *C12N 2310/20* (2017.05); *C12Y 205/01019* (2013.01)

(58) Field of Classification Search
None
See application file for complete search history.

(56) References Cited

U.S. PATENT DOCUMENTS

| | | |
|---|---|---|
| 5,500,360 A | 3/1996 | Ahlquist et al. |
| 5,736,369 A | 4/1998 | Bowen et al. |
| 6,187,994 B1 | 2/2001 | Baszczynski et al. |
| 6,410,329 B1 | 6/2002 | Hansen et al. |
| 6,603,061 B1 | 8/2003 | Armstrong et al. |
| 8,399,218 B2 | 3/2013 | Gupta et al. |
| 8,697,359 B1 | 4/2014 | Zhang |
| 2003/0135891 A1 | 7/2003 | Gould et al. |
| 2013/0263324 A1 | 10/2013 | Lassner |
| 2014/0068797 A1* | 3/2014 | Doudna ............... A01H 6/4684 800/18 |
| 2014/0170753 A1 | 6/2014 | Zhang |
| 2015/0059010 A1 | 2/2015 | Cigan |
| 2015/0067922 A1 | 3/2015 | Yang |
| 2016/0145631 A1 | 5/2016 | Voytas et al. |
| 2017/0260536 A1 | 9/2017 | Vainstein et al. |

FOREIGN PATENT DOCUMENTS

| | | |
|---|---|---|
| CN | 1541270 A | 10/2004 |
| CN | 102558309 A | 7/2012 |
| CN | 103343120 A | 10/2013 |
| CN | 2013/166315 A1 | 11/2013 |
| CN | 103382468 A | 11/2013 |
| CN | 103555711 A | 2/2014 |
| CN | 103667338 A | 3/2014 |
| DE | 10 2015 004 187 A1 | 10/2016 |
| EP | 2 274 973 A1 | 1/2011 |
| JP | 2010-539930 A | 12/2010 |
| KR | 1020150006469 | 1/2015 |

(Continued)

OTHER PUBLICATIONS

Chen & Gao (2013) J Genet & Genom 40(6):271-79.*
Zu et al. (2013) Nat Meth 10(4):329-31.*
Kanchiswamy et al. (2015) Trends Biotech 33(9):489-91.*
Carroll (2014) Annu Rev Biochem 83:409-39.*
Kumar & Jain (2015) J Exp Botany 66(1):37-57.*
International Search Report and Written Opinion issued by the International Searching Authority in International Application No. PCT/CN2016/095307, dated Nov. 23, 2016.
Weinthal, Dan Michael, "Nonhomologous End Joining-Mediated Gene Replacement in Plant Cells", Plant Physiology, May 31, 2013, vol. 162, pp. 390-400.
Xing at al., "A CRISPR/Cas9 toolkit for multiplex genome editing in the plants", BMC Plant Biology, 2014, vol. 14, pp. 327-338.

(Continued)

*Primary Examiner* — Russell T Boggs
(74) *Attorney, Agent, or Firm* — Troutman Pepper Hamilton Sanders LLP

(57) ABSTRACT

The present invention discloses a method for obtaining glyphosate-resistant rice by a site-directed nucleotide substitution, and also relates to a method capable of generating a site-directed nucleotide substitution and a fragment substitution. The method for obtaining a glyphosate-resistant plant provided by the present invention comprises the following steps: only substituting threonine (T) at position 8 of the amino acid sequence of a conserved region of endogenous EPSPS protein of a target plant with isoleucine (I), and substituting proline (P) at position 12 with serine (S) to obtain a plant, i.e., a glyphosate-resistant plant. The method provided by the present invention is of great significance in breeding new herbicide-resistant plant varieties. The present invention also discloses a method for utilizing a CRISPR-mediated NHEJ pathway to substitute a region between two gRNA sites by designing the two gRNA sites, thereby realizing a site-directed mutation of a target nucleotide and site-directed substitution of a fragment.

9 Claims, 8 Drawing Sheets
Specification includes a Sequence Listing.

(56) References Cited

FOREIGN PATENT DOCUMENTS

| WO | 00/66746 A1 | 9/2000 |
|---|---|---|
| WO | 2004/009761 A2 | 1/2004 |
| WO | 2009/042164 A1 | 4/2009 |
| WO | 2013/096567 | 6/2013 |
| WO | 2013/142578 A1 | 9/2013 |
| WO | 2013/169802 A1 | 11/2013 |
| WO | 2013/176772 A1 | 11/2013 |
| WO | 2014/144155 A1 | 9/2014 |
| WO | 2014/194190 A1 | 12/2014 |
| WO | 2015/026885 A1 | 2/2015 |
| WO | WO 2015/026886 A1 * | 2/2015 |
| WO | 2015/066637 A1 | 5/2015 |
| WO | 2015077290 A2 | 5/2015 |
| WO | 2016/021973 A1 | 2/2016 |
| WO | 2017/092201 A1 | 6/2017 |

OTHER PUBLICATIONS

Gilles et al., "Efficient CRISPR-mediated gene targeting and transgene replacement in the beetle *Tribolium castaneum*", Development, vol. 142, No. 16, 2015, pp. 2832-2839.

Li et al., "Gene replacements and insertions in rice by intron targeting using CRISPR-Cas9", Nature Plants, vol. 2, No. 10, 2016, Article No. 16139, 6 pages.

Supplementary Information for Zu et al., "TALEN-mediated precise genome modification by homologous recombination in zebrafish", Nature Methods, 2013, vol. 10, No. 4, pp. 329-331.

Armstrong et al., "Development and availability of germplasm with high Type II culture formation response", Maize Genet. Coop. News Lett., 1991, vol. 65, https://mnl.maizegdb.org/mnl/65/146armstrong.html. 3 pages.

Wang et al., "Simultaneous editing of three homoeoalleles in hexapioid bread wheat confers heritable resistance to powdery mildew", Nature Biotechnology, 2014, vol. 32, No. 9, pp. 947-952.

Weeks et al., "Rapid production of multiple independent lines of fertile transgenic wheat (*Triticum aestivum*)", Plant Physiol., 1993, vol. 102, pp. 1077-1084.

Shan et al., "Rapid and Efficient Gene Modification in Rice and Brachypodium Using TALENs", Molecular Plant, 2013, vol. 6, No. 4, pp. 1365-1368.

Gasiunas et al., "Cas9-crRNA ribonucleoprotein complex mediates specific DNA cleavage for adaptive immunity in bacteria", Proc. Natl Acad Sci USA, 2012, vol. 109, No. 39, pp. E2579-E2586.

Klein et al.,"Transformation of microbes, plants and animals by particle bombardment", Biotechnology, 1992, vol. 10, No. 3, pp. 286-291.

Jiang et al., "Efficient CRISPR/Cas9-mediated gene editing in *Arabidopsis thaliana* and inheritance of modified genes in the T2 and T3 generations", PloS one, 2014, vol. 9, Issue 6, pp. 1-10.

Shan et al., "Targeted genome modification of crop plants using a CRISPR-Cas System", Nature Biotechnology, vol. 31, No. 8, Aug. 1, 2013, pp. 686-688.

Shan et al., "Supplementary Material for Targeted genome modification of crop plants using a CRISPR-Cas system", Nature Biotechnology, vol. 31, No. 8, Aug. 1, 2013, 19 pages.

Zhang et al., "Transcription Activator-Like Effector Nucleases Enable Efficient Plant Genome Engineering", Plant Physiology, 2013, vol. 161, No. 1, pp. 20-27.

Kumar et al., "The CRISPR-Cas system for plant genome editing: advances and opportunities", Journal of Experimental Botany, 2015, vol. 66, No. 1, pp. 47-57.

Voytas et al., "Precision Genome Engineering and Agriculture: Opportunites and Regulatory Challenges", PLOS Biology, Jun. 2014, vol. 12, No. 6, e1001877, pp. 1-6.

Puchta et al., "Synthetic nucleases for genome engineering in plants prospects for a bright future", The Plant Journal, vol. 78, No. 5, 2014, pp. 727-741.

Marton et al., "Nontransgenic Genome Modification in Plant Cells", Plant Physiology, 2010, vol. 154, No. 3, pp. 1079-1087.

International Search Report and Written Opinion issued PCT/CN2016/071352, dated Apr. 25, 2016, 9 pages.

Ling et al., "Draft genome of the wheat A-genome progenitor *Triticum urartu*", Nature, 2013, vol. 496, pp. 87-90.

Shan et al., "Genome editing in rice and wheat using the CRISPR/Cas system", Nature Protocols, 2014, vol. 9, No. 10, pp. 2395-2410.

Mao et al., "Overexpression of a NAC-domain protein promotes shoot branching in rice", New Phytoiogist, 2007, vol. 176, pp. 288-298.

Xu et al., "A PIN1 Family Gene, OsPIN1, involved in Auxin-dependent Adventitious Root Emergence and Tillering in Rice", Plant Cell Physiol., 2005, vol. 46, No. 10, pp. 1674-1681.

Feng et al., "Molecular analysis of lipoxygenase (LOX) genes in common wheat and phylogenetic investigation of LOX proteins from model and crop plants", Journal of Cereal Science, 2010, vol. 52, pp. 387-394.

Lawrenson et al., "Induction of targeted, heritable mutations in barley and Brassica oleracea using RNA-guided Cas9 nuclease", Genome Biology, 2015, vol. 16, 258, 13 pages.

Zhang et al., "Biolistic Genetic Transformation of a Wide Range of Chinese Elite Wheat (*Triticum aestivum* L.) Varieties", Journal of Genetics and Genomics, 2015, vol. 42, pp. 39-42.

Larsen et al., "ALS3 encodes a phloem-localized ABC transporter-iike protein that is required for aluminum tolerance in *Arabidopsis*", The Plant Journal, 2005, vol. 41, No. 3, pp. 353-363.

Laursen et al., "Production of fertile transgenic maize by electroporation of suspension culture cells", Plant Molecular Biology, 1994, vol. 24, No. 1, pp. 51-61.

Aragao et al., "Particle bombardment-mediated transient expression of a Brazil nut methionine-rich albumin in bean (*Phaseolus vulgaris* L.)", Plant Molecular Biology, 1992, vol. 20, No. 2, pp. 357-359.

Brooks et al., "Efficient Gene Editing in Tomato in the First Generation Using the Clustered Regularly Interspaced Short Palindromic Repeats/CRISPR-Associated9 System", Plant Physiology, 2014, vol. 166, pp. 1292-1297.

International Search Report Issued in PCT/CN2016/072352 dated Apr. 27, 2016 and English Translation thereof 10 pages.

Russell, "Registration of B70 and B73 parental lines of maize", Crop Sci., 1972, vol. 12, p. 721.

Koomneef et ai., "Linkage map of *Arabidopsis thaliana*", The Journal of Heredity, 1983, vol. 74, pp. 265-272.

Li et al., "Multiplex and homologous recombination-mediated plant genome editing via guide RNA/Cas9", Nature Biotechnology, 2013, vol. 31, No. 8, pp. 688-691.

Written Opinion issued in PCT/CN2016/072352 dated Apr. 27, 2016 and English Translation thereof.

Luo et al., "A Simple Method for the Transformation of Rice via the Pollen-Tube Pathway", Plant Molecular Biology Reporter, 1988, vol. 6, No. 3, pp. 165-174.

Yang et al., "Transgenic soybean with low phytate content constructed by Agrobacterium transformation and pollen-tube pathway", Euphytlca, 2011, vol. 177, pp. 375-382.

Naito et al., "CRISPRdirect: software for designing CRISPR/Cas guide RNA with reduced off-target sites", Bioinfomatics, 2015, vol. 31, No. 7, pp. 1120-1123.

Basic knowledge of the database DIAM biotechnology, (a) Bioindustry Association, "Select temperature," URL:<http://togodb.biosciencedbc.jp/togodb/show/diam_bioterm_list/96>.

Ishida et al., "Agrobacterium-mediated transformation of maize", Nature Protocols, 2007, vol. 2, No. 7, pp. 1614-1621.

Xu et al., "Cloning of genomic DAN of rice 5-enolpyruvishikimate 3-phsphate synthase gene and chromosomal localization of the gene", Science in China, 2002, vol. 45, No. 3, pp. 251-259.

Doshi et al., "Anthocyanin expression in marker free transgenic wheat and triticale embryos", In Vitro Cell Dev. Biol.—Plant, 2007, vol. 43, pp. 429-435.

De Vetten et al., "A transformation method for obtaining marker-free plants of a cross-pollinating and vegetatively propagated crop", Nature Biotechnology, 2003, vol. 21, No. 4, pp. 439-442.

Pastori et al., "Age-dependent transformation frequency in elite wheat varieties", Journal of Experimental Botany, 2001, vol. 52, No. 357, pp. 857-863.

(56) References Cited

OTHER PUBLICATIONS

Elhiti et al., "The use of zygotic embryos as explants for in vitro propagation: an overview", Plant Embryo Culture:Methods and Protocols, Thrope et al. Eds., Methods in Molecular Biology, 2011, vol. 710, pp. 229-255.
Vasil et al., "Transformation of wheat via particle bombardment", Methods in Molecular Biology, 2006, vol. 318, pp. 273-283.
Jain et al., "TALEN outperforms Cas9 in editing heterochromatin target sites", Nature Communications, 2021, vol. 12, No. 606, 10 pages.
Zahir et al., "The Efficient Virus-Mediated Genome Editing in Plants Using the CRISPR/Cas9 System", Molecular Plant, vol. 8, No. 8, 2015, pp. 1288-1291.
Anonymous: "A Streamlined Method for the Production, Screening, and Application of sgRNAs for CRISPR/Cas9 Gene Editing" Bio Techniques, vol. 57, No. 3, Sep. 2014, p. 157.
Barrangou et al., "CRISPR provides acquired resistance against viruses in prokaryotes", Science, 2007, vol. 315, 1709-1712.
Zetsche et al., "Cpf1 is a single RNA-guided endonuclease of a Class 2 CRISPR-Cas system", Cell, vol. 163, No. 3, 2015, pp. 759-771.
Clough et al., "Floral Dip: a simplified method for Agrobacterium-mediated transformation of *Arabidopsis thaliana*", The Plant Journal, vol. 16, No. 6, 1998, pp. 735-743.
Deltcheva et al., "CRISPR RNA maturation by trans-encoded small RNA and host factor RNase III", Nature, 2011, vol. 471, No. 7340, pp. 602-607.
Gelvin, "Viral-mediated plant transformation gets a boost", Nature Biotechnology, vol. 23, No. 6, 2005, pp. 684-685.
Guilinger et al., "Fusion of catalytically inactive Cas9 to FokI nuclease improves the specificity of genome modification", Nat Biotechnol., 2014, vol. 32, No. 6, pp. 577-582.
Helenius et al., "Gene delivery into intact plants using the Helios Gene Gun", Plant Molecular Biology Reporter, 2000, vol. 18, No. 3, pp. 287a-287l.
International Search Report and Written Opinion issued in International Application No. PCT/EP2016/061237, dated Feb. 20, 2017.
Jansen et al., "Identification of genes that are associated with DNA repeats in pokaryotes", Molecular Microbiology, 2002, vol. 43, No. 6, pp. 1565-1575.
Jinek et al. "A programmable dual-RNA-guided DNA Endonuclease in Adaptive Bacterial Immunity", Science, 2012, vol. 337, pp. 816-821.
Kim et al., "Highly efficient RNA-guided genome editing in human cells via delivery of purified Cas9 ribonucleoproteins", Genome Research, 2014, vol. 24, No. 6, pp. 1012-1019.
Krens et al., "Transformation and regeneration in sugar beet (*Beta vulgaris* L.) induced by 'shooter' mutants of Agrobacterium tumefaciens", Euphytica, 1988, vol. 39, No. 3, pp. 185-194.
Leduc et al., "Gene transfer to Inflorescence and flower meristems using ballistic micro-targeting", Sexual Plant Reproduction, 1994, vol. 7, No. 2, pp. 135-143.
Bortesi et al., "The CRISPR/Cas9 system for plant genome editing and beyond", Biotechnology Advances, vol. 33, No. 1, Dec. 20, 2014, pp. 41-52.
Mahn et al., "Transient gene expression in shoot apical meristems of sugarbeet seedlings after particle bombardment", Journal of Experimental Botany, 1995, vol. 46, No. 291, pp. 1625-1628.
Makarova et al., "An updated evolutionary classification of CRISPR-Cas systems", Nature Rev. Microbiol., 2015, vol. 13, No. 11, pp. 722-736.
Makarova et al., "Annotation and Classification of CRISPR-Cas Systems", Methods Mol. Biol., 2015, vol. 1311, pp. 47-75.
Makarova et al., "Unification of Cas protein families and a simple scenario for the origin and evolution of CRISPR-Cas systems", Biology Direct, vol. 6, No. 38, 2011, 27 pages.
Mali et al., "CAS9 transcriptional activators for target specificity screening and paired nickases for cooperative genome engineering", Nat Biotechnol., 2013, vol. 31, No. 9, pp. 833-838.

Martin-Ortigosa et al., "Proteolistics: a biolistic method for intracellular delivery of proteins", Transgenic Research, 2014, vol. 23, pp. 743-756.
Baites et al., "DNA Replicons for Plant Genome Engineering" The Plant Cell, American Society of Plant Biologist, vol. 26, No. 1, Jan. 17, 2014, pp. 151-163.
Quinn et al., "A Streamlined Method for the Production, Screening, Application of sgRNAs for CRISPR/Cas Gene Editing", Molecular Therapy, vol. 22, Supplement 1, 2014, 2 pages.
Ramakrishna et al., "Gene disruption by cell-penetrating peptide-mediated delivery of Cas9 protein and guide RNA", Genome Research, 2014, vol. 24, No. 6, pp. 1020-1027.
Sapranauskas et al., "The *Streptococcus thermophilus* CRISPR/Cas system provides immunity in *Escherichia coli*", Nucleic Acids Research, 2011, vol. 39, No. 21, pp. 9275-9282.
Maruyama et al., "Inhibition of non-homologous end joining increases the efficiency of CRISPR/Cas9-mediated precise [TM: inserted] genome editing", Nat Biotechnol, vol. 33, No. 5, May 2015, pp. 538-542.
Jacobs et al., "Targeted genome modifications in soybean with CRISPR/Cas9", BMC Biotechnology, vol. 15, No. 16, 2015, pp. 1-10.
Van der Oost et al., "Unravelling the structural and mechanistic basis of CRISPR-Cas systems", Nat Rev Microbiol., 2014, vol. 12, No. 7, pp. 479-492.
Jiang et al., "Demonstration of CRISPR/Cas9/sgRNA-mediated targeted gene modification in *Arabidopsis*, tobacco, sorghum and rice", Nucleic Acids Research, 2013, vol. 41, No. 20, pp. e188, 12 pages total.
Wiedenheft et al., "Structures of the RNA-guided surveillance complex from a bacterial immune system", Nature, 2011, vol. 477, No. 7365, pp. 486-489.
Yoo et al., "*Arabidopsis mesophyll* protoplasts: a versatile cell system for transient gene expression analysis", Nature Protocols, 2007, vol. 2, No. 7, pp. 1565-1572.
Hyun et al. "Site-directed mutagenesis in *Arabidopsis thaliana* using dividing tissue-targeted RGEN of the CRISPR/Cas System to generate heritable null alleles". Planta, vol. 241, No. 1, Oct. 1, 2014, pp. 271-284.
Zhang et al., "The CRISPR/Cas9 System Produces Specific and Homozygous Targeted Gene Editing in Rice in One Generation," Plant Biotechnology Journal, 2014, vol. 12, No. 6, pp. 797-867.
International Search Report and Written Opinion issued by the International Searching Authority in International Application No. PCT/EP2016/061338, dated Aug. 5, 2016.
Abhishek et al., "Tissue Culture Independent Agrobacterium tumefaciens Mediated in Planta Transformation Method for Tropical Maize (*Zea mays.* L)", Proceedings of the National Academy of Sciences, India, Section B, Biological Sciences, 2016, vol. 86, No. 2, pp. 375-384.
Bent et al., "*Arabidopsis* in Planta Transformation. Uses, mechanisms, and Prospects for Transformation of Other Species", Plant Physiology, 2000, vol. 124, No. 4, p. 1540-1547.
Chowrira et al., "Transgenic Grain Legumes Obtained by in Planta Electroporation-Mediated Gene Transfer", Molecular Biotechnology, vol. 5, No. 2, 1996, pp. 85-96.
Razzaq et al., "Development of in planta transformation protocol for wheat", African Journal of Biotechnology, vol. 10, No. 5, 2011, pp. 740-756.
Collins et al., "The Effect of Cotyledon Excision on Reproductive Development in Pea (*Pisum sativum* L.)", Annals of Botany, vol. 38, No. 1, 1974, pp. 181-188.
Springer et al., "A Histological Examination of Tissue Culture Initiation From Immature Embryos of Maize",Protoplasma, 1979, vol. 101, pp. 269-281.
Ma et al., "Plant multiplex genome editing vector pYLCRISPR/Cas9P35s-B, complete sequence", GenBank KR 029113, 2015.
European Search Report issued in EP 15202060 dated Aug. 5, 2016.
Hu et al., "Agrobacterium-mediated vacuum infiltration and floral dip transformation of rapid-cycling Brassica rapa", BMC Plant Biology, 2019, vol. 19, Article No. 246, 9 pages.
Ghedira et al., "The Efficiency of *Arabidopsis thaliana* Floral Dip Transformation is Determined Not Only by the Agrobacterium

(56) References Cited

OTHER PUBLICATIONS

Strain Used but Also by the Physiology and the Ecotype of the Dipped Plant", MPMI, vol. 26, No. 7, 2013, pp. 823-832.

Takacs et al., "Ontogeny of the Maize Shoot Apical Meristem", The Plant Cell, vol. 24, Aug. 2012, pp. 3219-3234.

Al-Abed et al. "Split-seed: a new tool for maize researchers", Planta, 2006, vol. 223, pp. 1355-1360.

Feng et al., "Efficient genome editing in plants using a CRISPR/Cas System", Cell Research, 2013, vol. 23, No. 10, pp. 1229-1232.

Woo et al., "DNA-free genome editing in plants with preassembled CRISPR-Cas9 ribonucleoproteins," Nature Biotechnology, vol. 33, No. 11, 2015, pp. 1162-1165.

Liang et al., "Targeted Mutagenesis in *Zea mays* Using TALENs and the CRISPR/Cas System", Journal of Genetics and Genomics, 2013, vol. 41, No. 2, pp. 63-68.

Belhaj et al., "Editing plant genomes with CRISPR/Cas9", Current Opinion in Biotechnology, 2015, vol. 32, pp. 76-84.

\* cited by examiner

```
C3
WT : GTTTGGTTACTAAATATACAATCCCTTGGGTTTTAT (SEQ ID NO:27)
M1 : GTTTGGTTACTAAATATACAATCC..TGGGTTTTAT  -2 (SEQ ID NO:28)
M2 : GTTTGGTTACTAAATATACAAT........TTTTAT  -8 (SEQ ID NO:29)
M3 : GTTTGGTTACTAAATATAC........GTTTAT   -10 (SEQ ID NO:30)
M4 : GTTTGGTTACTAAATATACAATCCtCTTGGGTTTAT  +1 (SEQ ID NO:31)
```

C4
WT: TTATGAAAATATGTATGGAATTCATGGGGTATG (SEQ ID NO:32)
M1: TTATGAAAATATGTATGGAAT..ATGGGGTATG −2 (SEQ ID NO:33)
M2: TTATGAAAATATGTATGGAA..CATGGGGTATG −2 (SEQ ID NO:34)
M3: TTATGAAAATATGTATGGAA....TGGGGTATG −4 (SEQ ID NO:35)
M4: TTATGAAAATATGTATGGAATTCCATGGGGTATG +1 (SEQ ID NO:36)

Nucleotide sequence of OsEPSPS gene: CTCTTCTTGGGAACGCTGGAACTGCAATGGGAACCATTG (SEQ ID NO:1)

Encoded amino acid sequence: L F L G N A G T A M R P L (SEQ ID NO:2)

*FIG. 3A*

G  TACTAAATATACAATCCCTTGGG--CTCTTCTTGGGAACGCTGGAACTGCAATGCGACCATTG---AAAATATGTATGGAATTCATGGG (SEQ ID NO:39)

D  TACTAAATATACAATCCCTTGGG--CTCTTCTTGGGAACGCTGGAACTGCAATGCGATCGTTG---AAAATATGTATGGAATTCATGGG (SEQ ID NO:40)

1  TACTAAATATACAATCCCCTTGGG-CTCTTCTTGGGAACGCTGGAACTGCAATGCGATCGTTG---AAAATATGTATGGAA...TGGG +1, -4 (SEQ ID NO:41)

3  TACTAAATATACAATCC-CTTGGG-CTCTTCTTGGG-AACGCTGGAACTGCAATGCGACCATTG---AAAATATGTATGGAA..CATGGG +1, -2 (SEQ ID NO:42)

5  TACTAAATATACAATC..TTGGG--CTCTTCTTGGGAACGCTGGAACTGCAATGCGATCGTTG---AAAATATGTATGGAAT.CATGGG -2, -1 (SEQ ID NO:43)

6  TACTAAATATACAATC..TTGGG--CTCTTCTTGGGAACGCTGGAACTGCAATGCGAATTGCATGGG -2, +1 (SEQ ID NO:44)

7  TACTAAATATACAATCC.TTGGG--CTCTTCTTGGGAACGCTGGAACTGCAATGCGACCATTG---AAAATATG........CATGGG -1, -9 (SEQ ID NO:45)

8  TACTAA........CCCTTGGG--CTCTTCTTGGGAACGCTGGAACTGCAATGCGATCGTTG---AAAATATGTATGGAAT.CATGGG -9, -1 (SEQ ID NO:46)

*FIG. 4B*

SEQUENCE LISTING

```
<160> NUMBER OF SEQ ID NOS: 46

<210> SEQ ID NO 1
<211> LENGTH: 39
<212> TYPE: DNA
<213> ORGANISM: Oryza sativa

<400> SEQUENCE: 1
ctcttcttgg ggaacgctgg aactgcaatg cgaccattg                    39

<210> SEQ ID NO 2
<211> LENGTH: 13
<212> TYPE: PRT
<213> ORGANISM: Oryza sativa

<400> SEQUENCE: 2

Leu Phe Leu Gly Asn Ala Gly Thr Ala Met Arg Pro Leu
1               5                   10

<210> SEQ ID NO 3
<211> LENGTH: 1030
<212> TYPE: DNA
<213> ORGANISM: Oryza sativa

<400> SEQUENCE: 3
gtgagacgcg gatcccttcc tcttgcgtga attccatttc tggagatgag attttagggg      60
gtttattagg tgaggtggct gtgtttgtga aatcctagga attatctctc aagtcaatct     120
aacgatgaga tataactgag gttctggttt taatcacaca ctcatataac caatttattg     180
aaacattttg gtttggcata agaaactgct tacgaaggta tgatatcctc ctacatgtca     240
ggctactaaa ttttcacgac ggtatgatcc actcaaaaca agtttcttaa cgagtctggt     300
gaggtctgtt atgaaatttg tgtaaactaa ggcaactttg gaggtttcgc actgtaccaa     360
```

| | |
|---|---|
| tgttatgttt gaacattttg caagcagtgc tttctcccaa aattatgcaa ttttgaggct | 420 |
| cctctacatc attataattc cccaatacat tgctctttat tcttaatagc tttgatcgcg | 480 |
| aaatttaaca ttttaattct tgagctgtta ttttgtagca tcagtttatc atgagccatg | 540 |
| tttggtacta atatacaat cccttgggtt tatttgtttc caagcatgtc attaacttat | 600 |
| cttaatgtgg acaagaaact gatgcctgct tacattgcta ttatttcaag cgggtattga | 660 |
| tcctttgaca tgtgattgat cattttttt tctctggtta ttagggcaca acagtggtgg | 720 |
| acaacttgct gaacagtgag gatgttcact acatgcttga ggccctgaaa gccctcgggc | 780 |
| tctctgtgga agcagataaa gttgcaaaaa gagctgtagt cgttggctgt ggtggcaagt | 840 |
| ttcctgttga aaggatgcg aaagaggaag tgcaactctt cttggggaac gctggaactg | 900 |
| caatgcgacc attgacagca gccgtgactg ctgctggtgg aaatgcaacg tatgttttt | 960 |
| tttttaatgt ttatgaaaat atgtatggaa ttcatggggt atgttttatg acctttttct | 1020 |
| ttaccatcag | 1030 |

<210> SEQ ID NO 4
<211> LENGTH: 23
<212> TYPE: DNA
<213> ORGANISM: Oryza sativa

<400> SEQUENCE: 4

| | |
|---|---|
| tactaaatat acaatccctt ggg | 23 |

<210> SEQ ID NO 5
<211> LENGTH: 23
<212> TYPE: DNA
<213> ORGANISM: Oryza sativa

<400> SEQUENCE: 5

| | |
|---|---|
| aaaatatgta tggaattcat ggg | 23 |

<210> SEQ ID NO 6
<211> LENGTH: 1199
<212> TYPE: DNA
<213> ORGANISM: Artificial Sequence
<220> FEATURE:
<223> OTHER INFORMATION: mutation target sequence

<400> SEQUENCE: 6

| | |
|---|---|
| ccctctccga ggtgagacgc ggatcccttc ctcttgcgtg aattccattt ctggagatga | 60 |
| gatttaggg ggtttattag gtgaggtggc tgtgtttgtg aaatcctagg aattatctct | 120 |
| caagtcaatc taacgatgag atataactga ggttctggtt ttaatcacac actcatataa | 180 |
| ccaatttatt gaaacatttt ggtttggcat aagaaactgc ttacgaaggt atgatatcct | 240 |
| cctacatgtc aggctactaa attttcacga cggtatgatc cactcaaaac aagtttctta | 300 |
| acgagtctgg tgaggtctgt tatgaaattt gtgtaaacta aggcaacttt ggaggtttcg | 360 |
| cactgtacca atgttatgtt tgaacatttt gcaagcagtg ctttctccca aaattatgca | 420 |
| attttgaggc tcctctacat cattataatt ccccaataca ttgctcttta ttcttaatag | 480 |
| ctttgatcgc gaaatttaac attttaattc ttgagctgtt attttgtagc atcagtttat | 540 |
| catgagccat gtttggtact aaatatacaa tcccttgggt ttatttgttt ccaagcatgt | 600 |
| cattaactta tcttaatgtg gacaagaaac tgatgcctgc ttacattgct attatttcaa | 660 |
| gcgggtattg atcctttgac atgtgattga tcattttttt ttctctggtt attagggcac | 720 |
| aacagtggtg gacaacttgc tgaacagtga ggatgttcac tacatgcttg aggccctgaa | 780 |

```
agccctcggg ctctctgtgg aagcagataa agttgcaaaa agagctgtag tcgttggctg      840
tggtggcaag tttcctgttg agaaggatgc gaaagaggaa gtgcaactct tcttggggaa      900
cgctggaatt gcaatgcgat cgttgacagc agccgtgact gctgctggtg aaatgcaac       960 gtatgttttt ttttttaatg tttatgaaaa tatgtatgga attcatgggg tatgttttat     1020 gaccttttc tttaccatca gttatgtgct tgatggagtg ccacgaatga gggagagacc      1080
gattggtgac ttggttgtcg ggttgaaaca acttggtgcg gatgtcgact gtttccttgg     1140
cactgaatgc ccacctgttc gtgtcaaggg aattggagga cttcctggtg gcaaggtta     1199
```

```
<210> SEQ ID NO 7
<211> LENGTH: 13
<212> TYPE: PRT
<213> ORGANISM: Artificial Sequence
<220> FEATURE:
<223> OTHER INFORMATION: polypeptide of the mutated conserved region

<400> SEQUENCE: 7

Leu Phe Leu Gly Asn Ala Gly Ile Ala Met Arg Ser Leu
1               5                   10
```

```
<210> SEQ ID NO 8
<211> LENGTH: 1199
<212> TYPE: DNA
<213> ORGANISM: Oryza sativa

<400> SEQUENCE: 8
ccctctccga ggtgagacgc ggatcccttc ctcttgcgtg aattccattt ctggagatga       60
gattttaggg ggtttattag gtgaggtggc tgtgtttgtg aaatcctagg aattatctct      120
caagtcaatc taacgatgag atataactga ggttctggtt ttaatcacac actcatataa      180
ccaatttatt gaaacatttt ggtttggcat aagaaactgc ttacgaaggt atgatatcct      240
cctacatgtc aggctactaa attttcacga cggtatgatc cactcaaaac aagtttctta      300
acgagtctgg tgaggtctgt tatgaaattt gtgtaaacta aggcaacttt ggaggtttcg      360
cactgtacca atgttatgtt tgaacatttt gcaagcagtg cttctcccca aaattatgca      420
attttgaggc tcctctacat cattataatt ccccaataca ttgctcttta ttcttaatag      480
ctttgatcgc gaaatttaac attttaattc ttgagctgtt attttgtagc atcagtttat      540
catgagccat gtttggtact aaatatacaa tcccttgggt ttatttgttt ccaagcatgt      600
cattaactta tcttaatgtg gacaagaaac tgatgcctgc ttacattgct attatttcaa      660
gcgggtattg atcctttgac atgtgattga tcatttttt ttctctggtt attagggcac       720
aacagtggtg gacaacttgc tgaacagtga ggatgttcac tacatgcttg aggccctgaa      780
agccctcggg ctctctgtgg aagcagataa agttgcaaaa agagctgtag tcgttggctg      840
tggtggcaag tttcctgttg agaaggatgc gaaagaggaa gtgcaactct tcttggggaa      900
cgctggaact gcaatgcgac cattgacagc agccgtgact gctgctggtg aaatgcaac       960 gtatgttttt ttttttaatg tttatgaaaa tatgtatgga attcatgggg tatgttttat     1020 gaccttttc tttaccatca gttatgtgct tgatggagtg ccacgaatga gggagagacc      1080
gattggtgac ttggttgtcg ggttgaaaca acttggtgcg gatgtcgact gtttccttgg     1140
cactgaatgc ccacctgttc gtgtcaaggg aattggagga cttcctggtg gcaaggtta     1199
```

```
<210> SEQ ID NO 9
<211> LENGTH: 4950
```

<212> TYPE: DNA
<213> ORGANISM: Arabidopsis thaliana

<400> SEQUENCE: 9

| | | | | | |
|---|---|---|---|---|---|
| atggagatag | cttcttcttc | tggcagccgg | agatacgacg | ttttcccaag | ctttcgtgga | 60 |
| gaagatgtcc | gtgactcatt | cctcagccat | cttctcaagg | agctcagggg | caaagcaatc | 120 |
| acattcatag | atgatgagat | cgagaggagc | cgctcaatcg | gcccggagct | tttatcggca | 180 |
| ataaaagaat | cgagaatagc | aatcgttatc | ttctctaaga | actatgcttc | atccacctgg | 240 |
| tgcctgaatg | aattggtgga | gattcacaag | tgttatacga | atttgaatca | aatggtgatt | 300 |
| ccgattttct | tccacgttga | tgcttcggaa | gttaaaaaac | agaccggcga | atttggaaag | 360 |
| gtctttgaag | agacatgcaa | ggctaaatca | gaggatgaga | acaaagttg | gaagcaagct | 420 |
| ctagcagctg | ttgcagttat | ggccggatat | gatcttcgga | atggtatttt | caatgaatag | 480 |
| acttcgtgat | tttttttgttt | tgcgttgctt | ctttaatgaa | acagttgact | attgttatta | 540 |
| ggcctagtga | agcagccatg | attgaagagc | ttgccgagga | tgttttgaga | aaaactatga | 600 |
| caccatcgga | tgattttggc | gacttagtcg | gaattgaaaa | tcatatagag | gcaataaaat | 660 |
| cagtattgtg | cttggaatcc | aaggaagcta | gaataatggt | cgggatttgg | ggacaatcag | 720 |
| ggattggtaa | gagtaccata | ggaagagctc | tttacagtaa | actctctatc | cagttccacc | 780 |
| atcgcgcttt | cataacatat | aaaagcacca | gcggtagtga | cgtctctggc | atgaagttga | 840 |
| ggtgggaaaa | agaacttctc | tcggaaatct | taggtcaaaa | ggacataaag | atagagcatt | 900 |
| ttggtgtggt | ggagcaaagg | ttaaagcaac | agaaagttct | tatccttctt | gatgatgtgg | 960 |
| atagtctaga | gtttcttaag | accttggtgg | gaaaagctga | atggtttgga | tctggaagca | 1020 |
| gaataattgt | gatcactcaa | gataggcaac | ttctcaaggc | tcatgagatt | gaccttatat | 1080 |
| atgaggtgga | gttcccatct | gaacatcttg | ctcttacgat | gttatgccga | tctgcttttg | 1140 |
| ggaaagactc | tccacctgat | gattttaagg | aactagcatt | tgaagttgcg | aagcttgccg | 1200 |
| gtaatcttcc | gttgggtctt | agtgtccttg | gttcgtcttt | aaagggaagg | accaaagaat | 1260 |
| ggtggatgga | gatgatgcct | aggctccgaa | atggtttgaa | cggagatatt | atgaaaacat | 1320 |
| taagagtcag | ctacgataga | ttacatcaaa | aagatcaaga | tatgttcctt | tacatcgcgt | 1380 |
| gtttattcaa | tggttttgaa | gtcagttacg | tcaaagattt | acttaaagat | aatgttgggt | 1440 |
| ttacaatgtt | gactgagaag | tccctcatac | gtattcacac | cggatggatat | atagagatgc | 1500 |
| acaatttgct | agagaaattg | ggtagagaaa | ttgatcgtgc | aaagtccaag | ggtaatcctg | 1560 |
| gaaaacgtcg | atttctgacg | aattttgaag | atattcatga | agtagtgacc | gagaaaactg | 1620 |
| taagttttt | tcgcagctcc | gtttgaatgc | atgactttat | attaatataa | tcgtaatttg | 1680 |
| gggattgata | aacttaagca | attgttgcct | catgcgtaat | taaatgtag | ctttgatgtg | 1740 |
| tcagaaaatt | aaaaagggtt | gcgattgtta | agattatatt | agttttcttc | ggattttttt | 1800 |
| tcaggggaca | gaaactcttc | ttggaatacg | tttgccattc | gaggaatatt | tttcgacaag | 1860 |
| gccgttatta | atagataaag | aatcgttcaa | aggcatgcgt | aatctgcaat | atctagaaat | 1920 |
| tggttattac | ggggatctac | ctcagagcct | cgtttatttg | cccttaaac | tcagattgct | 1980 |
| agactgggat | gattgtccat | tgaagtcttt | gccatctact | tttaaggcgg | aatatctagt | 2040 |
| taacctcata | atgaagtata | gtaagcttga | gaaactgtgg | gaaggaactc | tggtacgaat | 2100 |
| tctaaatttt | attagttgtc | agttttagga | acagaactgt | ggtatatttg | tgaacgtgtg | 2160 |
| tattctcttt | ttccatattt | tgttttcagc | cccttggaag | tctcaaggag | atgaatttga | 2220 |

```
ggtattccaa caatttgaaa gaaattccag atctttcttt agccataaac ctcgaggaat    2280
tagatcttgt tggatgcaaa tctttggtga cacttccttc ctcgattcag aatgccacta    2340
aactgatcta tttagatatg agtgattgca aaaagctaga gagttttcca accgatctca    2400
acttggaatc tctcgagtac ctcaatctca ctggatgccc gaatttgaga aactttccag    2460
caatcaaaat gggatgttca gacgttgact ttccggaagg gagaaatgag atcgtggtag    2520
aagattgttt ctggaacaag aatctccctg ctggactaga ttatctcgac tgccttacga    2580
gatgtatgcc ttgtgaattt cgcccagaac aactcgcttt tctcaatgtg aggggctaca    2640
agcatgagaa gctatgggaa ggcatccagg tacattgtta atgctatgct gattttttgtt   2700 taccttctgt tatataacta attaactata cccaaatttg ttattatggc ttgtgatcca    2760
cggttatgtc ttaccacggt tatgtcttat aataatgttt aattataatt ttaaacatat    2820
acagtataaa attaaaatga ttatcatcga taatgattga agcataccaa tgttttttc     2880 agtcgcttgg aagtctcgaa gggatggatc tgtcagaatc tgaaaacctg acagaaattc    2940
cagatctttc aaaggccacc aagctcgagt ctttgatact caacaactgc aaaagtttgg    3000
tgacacttcc ttctacaatt gggaatcttc atagattggt gaggttggaa atgaaagaat    3060
gcacagggct ggaggttctt ccgaccgatg tcaacttgtc atctctcgaa accctcgatc    3120
tcagtggttg ctcaagtttg agaagttttc ctctgatttc aactaatatt gtatggctct    3180
atctggaaaa caccgccatt gaagaaattc cttctacaat tgggaatctt catagattgg    3240
tgaggttaga atgaaaaaa tgcacagggc tggaggttct tccgaccgat gtcaacttgt     3300
catctctcga aaccctcgat ctcagtggtt gctcaagttt gagaagtttt cctctgattt    3360
cagagagtat caaatggctc tatctggaaa acaccgccat tgaagaaatt ccagatcttt    3420
caaaggccac taatctgaag aatttgaaac tcaacaattg caaaagtttg gtgacacttc    3480
ctactactat aggaaatctc caaaaattgg tgagctttga atgaaagaa tgcacagggc     3540 tggaggttct tccgatcgat gtcaacttgt catctcttat gatcctcgat ctcagtggtt    3600
gctcaagtct gagaacttt cctctgattt caactaatat tgtatggctc tatctggaaa     3660
acaccgccat tgaagaaatc ccttctacaa ttgggaatct tcatagattg gtgaagttag    3720
aaatgaaaga atgcacaggg ctggaggttc ttccgaccga tgtcaacttg tcatctctta    3780
tgatcctcga tctcagtggt tgctcaagtc tgagaacttt tcctctgatt tcaactagaa    3840
tcgaatgtct ctatctgcaa acaccgcca ttgaagaagt tccctgctgc attgaggatt      3900
tcacgaggct cactgtactt atgatgtatt gttgccagag gttgaaaacc atctcccaa      3960 acattttcag acttacaaga cttgagctcg ccgactttac agactgtaga ggtgtcatca    4020
aggcgttgag tgatgcaact gtggtagcga caatggaaga ccacgtttct tgtgtaccat    4080
tatctgaaaa cattgaatat atctgggata agttgtatcg tgttgcatac ctccaggaac    4140
attttagctt ccgtaattgc ttcaaattgg atagagatgc gcgagagctc atcctacgat    4200
catgcttcaa gcctgtggcc ttaccaggtg aagaaatccc taagtatttc acgtatcgag    4260
cttatggaga ttccctaact gtcattgtac ctcagagctc tctttctcaa aatttcttgc    4320
gatttaaggc ttgcgtcgtg gttgaacctc tctccaaggg caagggtttt tatccattct    4380
tgaaggtaaa cgttggcttc aatggcaaac agtatcagaa atcattttct aaagatgcag    4440
aactggagct ttgtaagacg gatcatctgt ttttctgttc cttcaagttc cggtctgaag    4500
atcttccatc taaattgaat ttcaacgatg tggagtttaa gttttgttgc tccaatagga    4560
tcaaagaatg cggtgtacga ctcatgtatg tctctcaaga agagaacaac caacagacta    4620
```

```
cgagaagcga gaagcggatg cgggtatctt ttgactttg atttgatttt ccaggatcga     4680
aataccatag ggacagacta tttaatagaa tctatcgttt gatttataat gcagatgaca     4740
tcggggacat ctgaagaaga tatcaactta ccctatggcc taattgtagc ggacacagga     4800
ttggccgctc taaatatgga gctttcgtta gggcagggag aaccatcatc atcaacatct     4860 ctagagggg aagctttgtg tgttgattac atgataactg aagaacaaga taaggaatt      4920 cctatcttgt ttcctgtttc tggtaactga                                     4950
```

```
<210> SEQ ID NO 10
<211> LENGTH: 288
<212> TYPE: DNA
<213> ORGANISM: Artificial Sequence
<220> FEATURE:
<223> OTHER INFORMATION: Exon 3

<400> SEQUENCE: 10
gggacagaaa ctcttcttgg aatacgtttg ccattcgagg aatatttttc gacaaggccg      60
ttattaatag ataaagaatc gttcaaaggc atgcgtaatc tgcaatatct agaaattggt     120
tattacgggg atctacctca gagcctcgtt tatttgcccc ttaaactcag attgctagac     180
tgggatgatt gtccattgaa gtctttgcca tctacttta aggcggaata tctagttaac     240
ctcataatga agtatagtaa gcttgagaaa ctgtgggaag gaactctg                 288
```

```
<210> SEQ ID NO 11
<211> LENGTH: 288
<212> TYPE: DNA
<213> ORGANISM: Artificial Sequence
<220> FEATURE:
<223> OTHER INFORMATION: mutated exon 3

<400> SEQUENCE: 11
gggacagaaa ctcttcttgg aatacgtttg ccattcgagg aatatttttc gacaaggccg      60
ttattaatag ataaagaatc gttcaaaggc atgcgtaatc tgcaatatct aaaaattggt     120
tattacgggg atctacctca gagcctcgtt tatttgcccc ttaaactcag attgctagac     180
tgggatgatt gtccattgaa gtctttgcca tctacttta aggcggaata tctagttaac     240
ctcataatga agtatagtaa gcttgagaaa ctgtgggaag gaactctg                 288
```

```
<210> SEQ ID NO 12
<211> LENGTH: 23
<212> TYPE: DNA
<213> ORGANISM: Artificial Sequence
<220> FEATURE:
<223> OTHER INFORMATION: synthetic s1

<400> SEQUENCE: 12
cctcatgcgt aattaaaatg tag                                             23
```

```
<210> SEQ ID NO 13
<211> LENGTH: 23
<212> TYPE: DNA
<213> ORGANISM: Artificial Sequence
<220> FEATURE:
<223> OTHER INFORMATION: synthetic s2

<400> SEQUENCE: 13
cagtttttag aacagaactg tgg                                             23
```

```
<210> SEQ ID NO 14
```

```
<211> LENGTH: 435
<212> TYPE: DNA
<213> ORGANISM: Artificial Sequence
<220> FEATURE:
<223> OTHER INFORMATION: donor sequence

<400> SEQUENCE: 14
cctcatgcgt aattaaaatg tagctttgat gtgtcagaaa attaaaaagg gttgcgattg      60
ttaagattat attagttttc ttcggatttt ttttcagggg acagaaactc ttcttggaat     120
acgtttgcca ttcgaggaat attttttcgac aaggccgtta ttaatagata aagaatcgtt    180
caaaggcatg cgtaatctgc aatatctaaa aattggttat tacggggatc tacctcagag     240
cctcgtttat ttgcccctta aactcagatt gctagactgg gatgattgtc cattgaagtc     300
tttgccatct acttttaagg cggaatatct agttaacctc ataatgaagt atagtaagct     360
tgagaaactg tgggaaggaa ctctggtacg aattctaaat tttattagtt gtcagttttt     420
agaacagaac tgtgg                                                      435

<210> SEQ ID NO 15
<211> LENGTH: 24
<212> TYPE: DNA
<213> ORGANISM: Artificial Sequence
<220> FEATURE:
<223> OTHER INFORMATION: Synthetic forward primer for site in
      recombinant plasmid pHUN-411-C3

<400> SEQUENCE: 15
ggcgtactaa atatacaatc cctt                                             24

<210> SEQ ID NO 16
<211> LENGTH: 24
<212> TYPE: DNA
<213> ORGANISM: Artificial sequence
<220> FEATURE:
<223> OTHER INFORMATION: Synthetic reverse primer for site in
      recombinant plasmid pHUN-411-C3

<400> SEQUENCE: 16
aaacaaggga ttgtatattt agta                                             24

<210> SEQ ID NO 17
<211> LENGTH: 24
<212> TYPE: DNA
<213> ORGANISM: Artificial sequence
<220> FEATURE:
<223> OTHER INFORMATION: Synthetic forward primer for plasmid pHUN411-C4

<400> SEQUENCE: 17
ggcgaaaata tgtatggaat tcat                                             24

<210> SEQ ID NO 18
<211> LENGTH: 24
<212> TYPE: DNA
<213> ORGANISM: Artificial sequence
<220> FEATURE:
<223> OTHER INFORMATION: Synthetic reverse primer for plasmid pHUN411-C4

<400> SEQUENCE: 18
aaacatgaat tccatacata tttt                                             24

<210> SEQ ID NO 19
<211> LENGTH: 25
<212> TYPE: DNA
<213> ORGANISM: Artificial sequence
```

```
<220> FEATURE:
<223> OTHER INFORMATION: Synthetic forward primer for plasmid pHUN411-C3

<400> SEQUENCE: 19
ctaggaatta tctctcaagt caatc                                           25

<210> SEQ ID NO 20
<211> LENGTH: 22
<212> TYPE: DNA
<213> ORGANISM: Artificial sequence
<220> FEATURE:
<223> OTHER INFORMATION: Synthetic reverse primer for plasmid pHUN411-C3

<400> SEQUENCE: 20
ctcactgttc agcaagttgt cc                                              22

<210> SEQ ID NO 21
<211> LENGTH: 21
<212> TYPE: DNA
<213> ORGANISM: Artificial sequence
<220> FEATURE:
<223> OTHER INFORMATION: Synthetic forward primer for plasmid pHUN411-C4

<400> SEQUENCE: 21
ttcttaatag ctttgatcgc g                                               21

<210> SEQ ID NO 22
<211> LENGTH: 21
<212> TYPE: DNA
<213> ORGANISM: Artificial sequence
<220> FEATURE:
<223> OTHER INFORMATION: Synthetic reverse primer for plasmid pHUN411-C4

<400> SEQUENCE: 22
taaccttgcc accaggaagt c                                               21

<210> SEQ ID NO 23
<211> LENGTH: 19
<212> TYPE: DNA
<213> ORGANISM: Oryza sativa

<400> SEQUENCE: 23
ccctctccga ggtgagacg                                                  19

<210> SEQ ID NO 24
<211> LENGTH: 42
<212> TYPE: DNA
<213> ORGANISM: Artificial sequence
<220> FEATURE:
<223> OTHER INFORMATION: Synthetic forward primer for sequence on TB-
      EPSPS-D plasmid

<400> SEQUENCE: 24
gaacgctgga attgcaatgc gatcgttgac agcagccgtg ac                        42

<210> SEQ ID NO 25
<211> LENGTH: 40
<212> TYPE: DNA
<213> ORGANISM: Artificial sequence
<220> FEATURE:
<223> OTHER INFORMATION: Synthetic reverse primer for sequence on TB-
      EPSPS-D plasmid

<400> SEQUENCE: 25
tgctgtcaac gatcgcattg caattccagc gttccccaag                           40
```

<210> SEQ ID NO 26
<211> LENGTH: 21
<212> TYPE: DNA
<213> ORGANISM: Artificial sequence
<220> FEATURE:
<223> OTHER INFORMATION: Synthetic forward primer for sequence on TB-
      EPSPS-D plasmid

<400> SEQUENCE: 26
caacaggatc ctcctcctct c                                              21

<210> SEQ ID NO 27
<211> LENGTH: 34
<212> TYPE: DNA
<213> ORGANISM: Oryza sativa

<400> SEQUENCE: 27
gtttggtact aaatatacaa tcccttgggt ttat                                34

<210> SEQ ID NO 28
<211> LENGTH: 32
<212> TYPE: DNA
<213> ORGANISM: Oryza sativa

<400> SEQUENCE: 28
gtttggtact aaatatacaa tcctgggttt at                                  32

<210> SEQ ID NO 29
<211> LENGTH: 26
<212> TYPE: DNA
<213> ORGANISM: Oryza sativa

<400> SEQUENCE: 29
gtttggtact aaatatacaa ttttat                                         26

<210> SEQ ID NO 30
<211> LENGTH: 24
<212> TYPE: DNA
<213> ORGANISM: Oryza sativa

<400> SEQUENCE: 30
gtttggtact aaatatacgt ttat                                           24

<210> SEQ ID NO 31
<211> LENGTH: 35
<212> TYPE: DNA
<213> ORGANISM: Oryza sativa

<400> SEQUENCE: 31
gtttggtact aaatatacaa tcctcttggg tttat                               35

<210> SEQ ID NO 32
<211> LENGTH: 33
<212> TYPE: DNA
<213> ORGANISM: Oryza sativa

<400> SEQUENCE: 32
ttatgaaaat atgtatggaa ttcatggggt atg                                 33

<210> SEQ ID NO 33
<211> LENGTH: 31
<212> TYPE: DNA
<213> ORGANISM: Oryza sativa

```
<400> SEQUENCE: 33
ttatgaaaat atgtatggaa tatggggtat g                                    31

<210> SEQ ID NO 34
<211> LENGTH: 31
<212> TYPE: DNA
<213> ORGANISM: Oryza sativa

<400> SEQUENCE: 34
ttatgaaaat atgtatggaa catggggtat g                                    31

<210> SEQ ID NO 35
<211> LENGTH: 29
<212> TYPE: DNA
<213> ORGANISM: Oryza sativa

<400> SEQUENCE: 35
ttatgaaaat atgtatggaa tggggtatg                                       29

<210> SEQ ID NO 36
<211> LENGTH: 34
<212> TYPE: DNA
<213> ORGANISM: Oryza sativa

<400> SEQUENCE: 36
ttatgaaaat atgtatggaa ttccatgggg tatg                                 34

<210> SEQ ID NO 37
<211> LENGTH: 39
<212> TYPE: DNA
<213> ORGANISM: Oryza sativa

<400> SEQUENCE: 37
ctcttcttgg ggaacgctgg aattgcaatg cgatcgttg                            39

<210> SEQ ID NO 38
<211> LENGTH: 13
<212> TYPE: PRT
<213> ORGANISM: Oryza sativa

<400> SEQUENCE: 38

Leu Phe Leu Gly Asn Ala Gly Ile Ala Met Arg Ser Leu
1               5                   10

<210> SEQ ID NO 39
<211> LENGTH: 85
<212> TYPE: DNA
<213> ORGANISM: Oryza sativa

<400> SEQUENCE: 39
tactaaatat acaatccctt gggctcttct tggggaacgc tggaactgca atgcgaccat     60
tgaaaatatg tatggaattc atggg                                           85

<210> SEQ ID NO 40
<211> LENGTH: 85
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 40
tactaaatat acaatccctt gggctcttct tggggaacgc tggaattgca atgcgatcgt     60
```
tgaaaatatg tatggaattc atggg                                              85

<210> SEQ ID NO 41
<211> LENGTH: 82
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 41
tactaaatat acaatcccct tgggctcttc ttggggaacg ctggaattgc aatgcgatcg        60
ttgaaaatat gtatggaatg gg                                                 82

<210> SEQ ID NO 42
<211> LENGTH: 84
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 42
tactaaatat acaatcccct tgggctcttc ttggggaacg ctggaactgc aatgcgacca        60
ttgaaaatat gtatggaaca tggg                                               84

<210> SEQ ID NO 43
<211> LENGTH: 82
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 43
tactaaatat acaatcttgg gctcttcttg gggaacgctg gaattgcaat gcgatcgttg        60
aaaatatgta tggaatcatg gg                                                 82

<210> SEQ ID NO 44
<211> LENGTH: 84
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 44
tactaaatat acaatcttgg gctcttcttg gggaacgctg gaactgcaat gcgaccattg        60
aaaatatgta tggaattaca tggg                                               84

<210> SEQ ID NO 45
<211> LENGTH: 75
<212> TYPE: DNA
<213> ORGANISM: Artificial Sequence
<220> FEATURE:
<223> OTHER INFORMATION: Oryza sativa L. japonica cv. Nipponbare

<400> SEQUENCE: 45
tactaaatat acaatccttg ggctcttctt ggggaacgct ggaactgcaa tgcgaccatt        60
gaaaatatgc atggg                                                         75

<210> SEQ ID NO 46
<211> LENGTH: 75
<212> TYPE: DNA
<213> ORGANISM: Artificial Sequence
<220> FEATURE:
<223> OTHER INFORMATION: Oryza sativa L. japonica cv. Nipponbare

```
<400> SEQUENCE: 46
tactaaccct tgggctcttc ttggggaacg ctggaattgc aatgcgatcg ttgaaaatat      60
gtatggaatc atggg                                                      75
```

METHOD FOR OBTAINING GLYPHOSATE-RESISTANT RICE BY SITE-DIRECTED NUCLEOTIDE SUBSTITUTION

CROSS-REFERENCE TO RELATED APPLICATIONS

This application is a U.S. National Stage of International Patent Application No. PCT/CN2016/095307 filed Aug. 15, 2016, which claims the benefit of Chinese Patent Application No. 201510200930.8 filed Aug. 14, 2015, both of which applications are herein incorporated by reference in their entireties.

SEQUENCE LISTING

The instant application contains a Sequence Listing which has been submitted in ASCII format via EFS-Web and is hereby incorporated by reference in its entirety. Said ASCII copy, created on Nov. 13, 2018, is named 241957.000053.sequence_ST25.TXT, and is 21,483 bytes in size.

TECHNICAL FIELD

The present invention belongs to the field of biotechnological breeding, relates to a method for obtaining glyphosate-resistant rice by site-directed nucleotide substitution, and also relates to a method for generating site-directed nucleotide substitution and fragment substitution.

BACKGROUND

Rice is the main food crop in China and even the world. In our country, the total area, total yield and yield per unit area of rice top the list, and the planting area is about 500 million mu. In China, the paddy weeds occurrence area accounts for about 45% of the rice planting area. The yield of the rice is generally reduced by 5% to 15% in the absence of weed control, resulting in a loss about 10 million tons every year. In some severe situation, the yield may be reduced by 15% to 30%. In order to control paddy weeds, a lot of manpower and material resources and financial resources were input, and also a large amount of herbicide was applied. Therefore, it is of vital importance to develop herbicide-resistant rice. Traditional breeding is time-consuming, and the available germplasm resources are deficient. With the development of transgenic technology and genome editing technology, an effective way is provided for the breeding of glyphosate resistance rice.

The genome editing technology is a rising new technology in recent years, and mainly includes three types of sequence specific nucleases: zinc finger nuclease (ZFN), transcription activator-like effector nuclease (TALEN) and clustered regularly interspaced short palindromic repeats/CRISPR associated (CRISPR/Cas9) system. These artificial nucleases can generate DNA double-strand breaks (DSBs) at DNA target sites, and the DSBs generated after damage of DNA activate intracellular inherent non-homologous ending-joining (NHEJ) or homologous recombination (HR) as two different repair mechanisms to repair the damaged DNA: the probability of repair by HR is very low; the organism is mainly repaired by the NHEJ, where the broken chromosome will be re-joined, but the joining is usually not accurate, and the insertion or deletion of a few nucleotides will be generated at the break positions, resulting in a frameshift mutation or early termination of protein translation, thus realizing the site-directed knockout of a target gene.

Glyphosate is a nonselective herbicide with the advantages of broad spectrum, high efficiency, low toxicity and low residue, nonselective for the majority of plants, and is the herbicide mostly used in the world currently. Its mechanism of action mainly lies in competitively inhibiting the activity of 5-enolpyruvylshikimate-3-phosphate synthase (EPSPS) in the shikimic acid pathway, resulting in the block of aromatic amino acid synthesis, and eventually killing the plants.

SUMMARY OF THE INVENTION

The present invention discloses a method for obtaining a glyphosate-resistant plant.

The method for obtaining the glyphosate-resistant plants provided by the present invention comprises the following steps: only substituting threonine (T) at position 8 of the amino acid sequence of a conserved region of endogenous EPSPS protein of a target plant with isoleucine (I), and substituting proline (P) at position 12 with serine (S) to obtain a plant, i.e., a glyphosate-resistant plant; the amino acid sequence of the conserved region of the endogenous EPSPS protein of the target plant is set forth in SEQ ID No. 2.

The amino acid sequence of the conserved region obtained after the substitution is set forth in SEQ ID No. 7.

According to the method, the steps of "only substituting threonine (T) at position 8 of the amino acid sequence of a conserved region of endogenous EPSPS protein of a target plant with isoleucine (I), and substituting proline (P) at position 12 with serine (S)" are realized by introducing the following a), b), c), d), e) or f) into a cell or tissue of the target plant, and then culturing the cell or tissue as obtained into complete plants;

a) a genetic material 1, a genetic material 2 and a donor vector: the genetic material 1 is a circular DNA plasmid, a linear DNA fragment or an RNA transcribed in vitro capable of expressing a sequence specific nuclease 1; the genetic material 2 is a circular DNA plasmid, a linear DNA fragment or an RNA transcribed in vitro capable of expressing a sequence specific nuclease 2;

b) a genetic material 12 and a donor vector: the genetic material 12 is a circular DNA plasmid, a linear DNA fragment or an RNA transcribed in vitro capable of expressing the sequence specific nuclease 1 and also expressing the sequence specific nuclease 2;

c) a non-genetic material 1, a non-genetic material 2 and a donor vector: the non-genetic material 1 is an mRNA capable of expressing the sequence specific nuclease 1; the non-genetic material 2 is an mRNA capable of expressing the sequence specific nuclease 2;

d) a non-genetic material 1, a non-genetic material 2 and a donor vector: the non-genetic material 1 is the protein of the sequence specific nuclease 1 expressed in vitro; the non-genetic material 2 is the protein of the sequence specific nuclease 2 expressed in vitro;

e) a donor vector;

f) a donor vector capable of expressing the sequence specific nuclease 1 and also capable of expressing the sequence specific nuclease 2;

the donor vector is a vector carrying a mutation target sequence; the mutation target sequence contains a DNA fragment sequence corresponding to a sequence in the genome of the target plant from the 5' end of a target fragment 1 to the 3' end of a target fragment 2, which contains the desired nucleotide mutation; the target fragment 1 is positioned in an intron region (denoted as intron region 1) or a promoter region in the genome of the target plant upstream of the nucleotide sequence encoding the amino acid sequence of the conserved region of the endogenous EPSPS protein; the target fragment 2 is positioned in an intron region (denoted as intron region 2) or a 3'-UTR region in the genome of the target plant downstream of a nucleotide sequence encoding the amino acid sequence of the conserved region of the endogenous EPSPS protein; the nucleotide mutation is a mutation by which threonine (T) at position 8 of the amino acid sequence of the conserved region of endogenous EPSPS protein of a target plant is substituted with isoleucine (I), and proline (P) at position 12 is substituted with serine (S).

The mutation target sequence may be a DNA fragment sequence corresponding to a sequence in the genome of the target plant from the 5' end of a target fragment 1 to the 3' end of a target fragment 2, which contains the desired nucleotide mutation; and may further contains an upstream and/or downstream homologous sequence, wherein the upstream homologous sequence is a segment of sequence positioned in the upstream of the target fragment 1 in the genome of the target plant, the downstream homologous sequence is a segment of sequence positioned in the downstream of the target fragment 2 in the genome of the target plant.

The sequence specific nuclease 1 is able to specifically cleave the target fragments 1 in the genome of the target plant and the donor vector; the sequence specific nuclease 2 is able to specifically cleave the target fragments 2 in the genome of the target plant and the donor vector; when the sequence specific nuclease 1 and the sequence specific nuclease 2 cleave the target fragments 1 and the target fragments 2 in the genome of the target plant and the donor vector at the same time, the fragment containing the substituted nucleotide between two target sites of the donor vector can be inserted between the two target sites of the genome of the target plant, thus obtaining a genome sequence with a site-directed nucleotide substitution.

The sequence specific nuclease (such as the sequence specific nuclease 1 or the sequence specific nuclease 2) specifically cleaves the target fragments in the genome of the target plant and the donor vector at the same time, which possibly results in an insertion mutation, and/or a deletion mutation of several nucleotides, but such mutation is positioned in the prompter region, and/or intron region, and/or UTR region (Untranslated Region), and thus generally the function of the protein will not be affected; when the two sequence specific nucleases (such as the sequence specific nuclease 1 or the sequence specific nuclease 2) cleave the target fragments 1 and the target fragments 2 in the genome of the target plant and the donor vector at the same time, a nucleotide substitution mutation of the sequence between two target sites can be generated.

Both the sequence specific nuclease 1 and the sequence specific nuclease 2 may be a CRISPR/Cas9 nuclease, a TALEN nuclease, a zinc finger nuclease or any sequence specific nuclease capable of realizing genome editing; the sequence specific nuclease 1 and the sequence specific nuclease 2 may be of the same type or may be of different type.

According to the method, the plant may be a monocotyledon or dicotyledon. The monocotyledon may be a gramineous plant. Specifically, the gramineous plant may be rice.

In an embodiment of the present invention, specifically, the plant is rice (Oryza sativa L. japonica. cv. Nipponbare).

Accordingly, at the genomic DNA level, the residues to be mutated (position 8 and position 12) in the amino acid sequence of the conserved region of the endogenous EPSPS protein of the target plant are positioned in the second exon of the endogenous EPSPS protein of the target plant; the intron region 1 is the first intron, the nucleotide sequence of which corresponds to position 1-704 of SEQ ID No. 3 in the sequence listing; the intron region 2 is the second intron, the nucleotide sequence of which corresponds to position 950-1030 of SEQ ID No. 3 in the sequence listing. Both the sequence specific nuclease 1 and the sequence specific nuclease 2 are CRISPR/Cas9 nucleases, and the target fragment 1 is a fragment complying with the formula 5'-$N_X$-NGG-3' or 5'-CCN-$N_X$-3' within the nucleotide sequence corresponds to position 1-704 of SEQ ID No. 3 in the sequence listing; N represents any one of A, G, C, and T; 14≤X≤30 and X is an integer (e.g., X is 20); and $N_X$ represents X consecutive nucleotides. The target fragment 2 is a fragment complying with the formula 5'-$N_X$-NGG-3' or 5'-CCN-$N_X$-3' within the nucleotide sequence corresponds to position 950-1030 of SEQ ID No. 3 in the sequence listing; N represents any one of A, G, C, and T; 14≤X≤30 and X is an integer (e.g., X is 20); and $N_X$ represents X consecutive nucleotides.

Furthermore, the nucleotide sequence of the target fragment 1 is set forth in SEQ ID No. 4 in the sequence listing; the nucleotide sequence of the target fragment 2 is set forth in SEQ ID No. 5 in the sequence listing.

Accordingly, according to the present invention, specifically, the genetic material 1 is a recombinant plasmid (pHUN411-C3) obtained by substituting the small fragment between two restriction enzymes BsaI of the pHUN411 vector with a DNA fragment corresponds to position 1-20 of SEQ ID No. 4 in the sequence listing; specifically, the genetic material 2 is a recombinant plasmid (pHUN411-C4) obtained by substituting the small fragment between two restriction enzymes BsaI of the pHUN411 vector with a DNA fragment corresponds to position 1-20 of SEQ ID No. 5 in the sequence listing.

Specifically, the nucleotide sequence of the mutation target sequence carried by the donor vector is SEQ ID No. 6 in the sequence listing. Specifically, the donor vector is a recombinant plasmid (pEPSPS-donor) obtained by inserting a DNA fragment shown in SEQ ID No. 6 No. 6 in the sequence listing into a pEASY-Blunt vector (TransGen Biotech Co., Ltd, catalogue number: CB101)

According to the present invention, the pHUN411-C3, the pHUN411-C4 and the pEPSPS-donor are introduced into rice calluses (Oryza sativa L. japonica. cv. Nipponbare), at a molar ratio of 1:1:2.

According to the method, the cell may be any cell that can be used as an introduction recipient and can be regenerated into a complete plant by tissue culture; the tissue may be any cell that can be used as an introduction recipient and can be regenerated into a complete plant by tissue culture. Specifically, for example, the cell may be a protoplast cell or suspension cell; for example, the tissue may be callus, immature embryo or mature embryo.

According to the method, the approach for introducing a), b), c), d) or e) into the cell or tissue of the target plant may be a gene gun approach, an Agrobacterium infection approach, a PEG-mediated protoplast transformation approach or any other introduction approach.

Any one of the following biological materials also falls within the protection scope of the present invention:

(1) a protein formed by only substituting threonine (T) at position 8 of the amino acid sequence of a conserved region of rice endogenous EPSPS protein with isoleucine (I), and substituting proline (P) at position 12 with serine (S); the amino acid sequence of the conserved region of the rice endogenous EPSPS protein is SEQ ID No. 2 in the sequence listing;

(2) a coding gene of said protein;

(3) an expression cassette recombinant vector, recombinant bacterium or transgenic cell line containing said coding gene.

Said transgenic cell line is a non-propagating material.

The present invention also provide a method for substituting a target nucleotide in a target gene, wherein the target nucleotide may be one or more non-consecutive nucleotides, and may also be a fragment formed by a plurality of consecutive nucleotides.

In the method for substituting a target nucleotide in a target gene, the step of substituting the target nucleotide in the target gene of a target organism is realized by introducing the following a), b), c), d) or e) into a cell or tissue of the target organism:

a) a genetic material 1, a genetic material 2 and a donor vector: the genetic material 1 is a circular DNA plasmid, a linear DNA fragment or an RNA transcribed in vitro capable of expressing a sequence specific nuclease 1; the genetic material 2 is a circular DNA plasmid, a linear DNA fragment or an RNA transcribed in vitro capable of expressing a sequence specific nuclease 2;

b) a genetic material 12 and a donor vector: the genetic material 12 is a circular DNA plasmid, a linear DNA fragment or an RNA transcribed in vitro capable of expressing the sequence specific nuclease 1 and also expressing the sequence specific nuclease 2;

c) a non-genetic material 1, a non-genetic material 2 and a donor vector: the non-genetic material 1 is an mRNA capable of expressing the sequence specific nuclease 1; the non-genetic material 2 is an mRNA capable of expressing the sequence specific nuclease 2;

d) a non-genetic material 1, a non-genetic material 2 and a donor vector: the non-genetic material 1 is a protein of the sequence specific nuclease 1 expressed in vitro; the non-genetic material 2 is a protein of the sequence specific nuclease 2 expressed in vitro;

e) a donor vector capable of expressing the sequence specific nuclease 1 and also expressing the sequence specific nuclease 2;

the donor vector is a vector carrying a mutation target sequence; the mutation target sequence contains a DNA fragment sequence corresponding to a sequence in the genome of the target organism from the 5' end of a target fragment 1 to the 3' end of a target fragment 2, which contains the desired nucleotide substitution; the target fragment 1 is positioned in an intron region or a promoter region upstream the target nucleotide of the target gene in the genome of the target organism; the target fragment 2 is positioned in an intron region or a 3'-UTR region downstream the target nucleotide of the target gene in the genome of the target organism. The target sites of the two sequence specific nucleases are positioned in the prompter region, and/or the intron region, and/or a UTR region (Untranslated Untranslated Region), and the expression of the target genet generally will not be affected by an insertion and a deletion of a small number of nucleotides in such regions.

The mutation target sequence may be a DNA fragment sequence corresponding to a sequence in the genome of the target organism from the 5' end of a target fragment 1 to the 3' end of a target fragment 2, which contains the desired nucleotide substitution; and may further contains an upstream and/or downstream homologous sequence, wherein the upstream homologous sequence is a segment of sequence positioned in the upstream of the target fragment 1 in the genome of the target organism, the downstream homologous sequence is a segment of sequence positioned in the downstream of the target fragment 2 in the genome of the target organism.

The sequence specific nuclease 1 is able to specifically cleave the target fragments 1 in the genome of the target organism and the donor vector; the sequence specific nuclease 2 is able to specifically cleave the target fragments 2 in the genome of the target organism and the donor vector. The donor vector is directed to the target gene in the genome of the target organism by the upstream and downstream homologous sequences in the donor vector. When the sequence specific nuclease 1 and the sequence specific nuclease 2 cleave the target fragments 1 and the target fragments 2 in the genome of the target organism and the donor vector at the same time, a fragment containing the nucleotide to be substituted between two target sites of the donor vector can be inserted between the two target sites of the genome of the target organism, thus obtaining a genome sequence with a site-directed nucleotide substitution.

The target organism may be a target plant, target animal or target microorganism. Both the sequence specific nuclease 1 and the sequence specific nuclease 2 may be a CRISPR/Cas9 nuclease, a TALEN nuclease, a zinc finger nuclease or any sequence specific nuclease capable of realizing genome editing. The sequence specific nuclease 1 and the sequence specific nuclease 2 may be of the same type and may also be of different types.

In some embodiments, said target organism is a plant, including monocotyledon or dicotyledon, such as rice or *Arabidopsis*. The cell may be any cell that can be used as an introduction recipient and can be regenerated into a complete plant by tissue culture; the tissue may be any cell that can be used as an introduction recipient and can be regenerated into a complete plant by tissue culture. Specifically, for example, the cell may be a protoplast cell or suspension cell; for example, the tissue may be callus, immature embryo or mature embryo. The approach for introducing a), b), c), d) or e) into the cell or tissue of the target plant may be a gene gun approach, an *Agrobacterium* infection approach, a PEG-mediated protoplast transformation approach or any other introduction approach.

In one specific embodiment, said plant is *Arabidopsis*; said target gene is Atsnc1(At4g16890) of SEQ ID NO.9; said sequence specific nuclease 1 comprises a sgDNA corresponding to SEQ ID NO.12; said sequence specific nuclease 2 comprises a sgDNA corresponding to SEQ ID NO.13; said mutation target sequence is set forth in SEQ ID NO.14; substitution of the target nucleotide results in the replacement of Exon 3 of Atsnc1 of SEQ ID NO.10 with SEQ ID NO.11, and thus conferring the plant the resistance against *Pseudomonas syringae* pv *maculicola* ES4326 and *Peronospora parasitica* Noco2.

In the present invention, according to the CRISPR-mediated NHEJ pathway, two gRNA sites respectively positioned in the first intron and the second intron of EPSPS gene are designed, the two gRNAs cleave the target fragments 1 and 2 in the genome and the donor vector at the same time through CRISPR/Cas9 technology, a fragment corresponding to the sequence between the target sites in which the nucleotide(s) is substituted has a chance to be inserted between the target sites in the genome to substitute the second exon of rice, so that the site-directed mutation of two amino acids in the conserved region is realized, and thus rice with glyphosate resistance is produced. It is of great significance in breeding new herbicide-resistant plant varieties.

The present invention also provides a method for site-directed substitution of a target nucleotide in a target gene.

BRIEF DESCRIPTION OF THE DRAWINGS

FIG. 2A shows the PCR/RE detection results of the target site C3 in the protoplast. FIG. 2A shows the corresponding sequencing results of the target site C3. FIG. 2B discloses SEQ ID NOS: 27-31, respectively, in order of appearance. FIG. 2C shows the PCR/RE detection results of the target site C4 in the protoplast. FIG. 2D shows the corresponding sequencing results of the target site C4. FIG. 2D discloses SEQ ID NOS: 32-36, respectively, in order of appearance. WT represents a genomic sequence of wild-type rice (*Oryza sativa L. japonica.* cv. Nipponbare), "−" represents a deletion mutation, "+" represents an insertion mutation, the number after "−/+" represents the number of deleted or inserted nucleotides (lowercase letters represent inserted nucleotides), and M1 to M4 represent four mutation types.

FIGS. 3A and 3B are schematic diagrams showing the structure of a donor vector (pEPSPS—donor) containing substitutions. FIG. 3A shows a DNA sequence in a conserved region of EPSPS in a genome of rice (SEQ ID NO: 1) and the coded amino acid sequence of the conserved region (SEQ ID NO: 2). FIG. 3B shows the DNA sequence (SEQ ID NO: 37) and the coded amino acid sequence of the conserved region of EPSPS (SEQ ID NO: 38) in the donor vector, and the amino acid in bold is a substitution amino acid. To facilitate the later detection, an enzyme site PvuI is obtained by a synonymous mutation.

FIGS. 4A and 4B show the detection of T0-generation mutants of CRISPR-mediated site-directed mutation rice OsEPSPS gene by using PCR/RE and the sequencing results. FIG. 4A shows the PCR/RE detection results of the T0-generation mutants, wherein 1 to 16 are different regeneration lines, PCR product is cleaved by using PvuI restriction enzymes, ck is a control of wild type rice (*Oryza sativa L. japonica.* cv. Nipponbare) FIG. 4B shows sequencing results of mutants 1, 5 and 7, wherein G represents a partial sequence of an EPSPS gene of the wild type rice (*Oryza sativa L. japonica.* cv. Nipponbare): the left sequence is a C3 site sequence, the middle is a DNA sequence in the conserved region of EPSPS, and the right is a C4 site sequence; D represents a partial sequence of an EPSPS gene of the donor vector: the left sequence is a C3 site sequence, the middle sequence is a DNA sequence in the conserved region of EPSPS with site-directed mutations, and the right sequence is a C4 site sequence. FIG. 4B discloses SEQ ID NOS: 39-46, respectively, in order of appearance. "−" represents a deletion mutation, "+" represents an insertion mutation, the number after "−/+" represents the number of deleted or inserted nucleotides (lowercase letters represent inserted nucleotides).

DETAILED DESCRIPTION OF THE PREFERRED EMBODIMENTS

Unless otherwise specified, experimental methods used in the following examples are all conventional methods.

Unless otherwise specified, materials, reagents, etc. used in the following examples are commercially available.

pHUN411 vector: disclosed in a literature "Hui-Li Xing, Li Dong, Zhi-Ping, Wang Hai-Yan Zhang, Chun-Yan Han, Bing, Liu Xue-Chen Wang, Qi-Jun Chen. A CRISPR/Cas9 toolkit for multiplex genome editing in the plants. The BMC plant biology. 14: 327-338 (2014)", and can be obtained by the public from the Institute of Genetics and Developmental Biology, Chinese Academy of Sciences. The plasmid can be used for transcribing a guide RNA and expressing a Cas9 protein at the same time.

Figure 1:
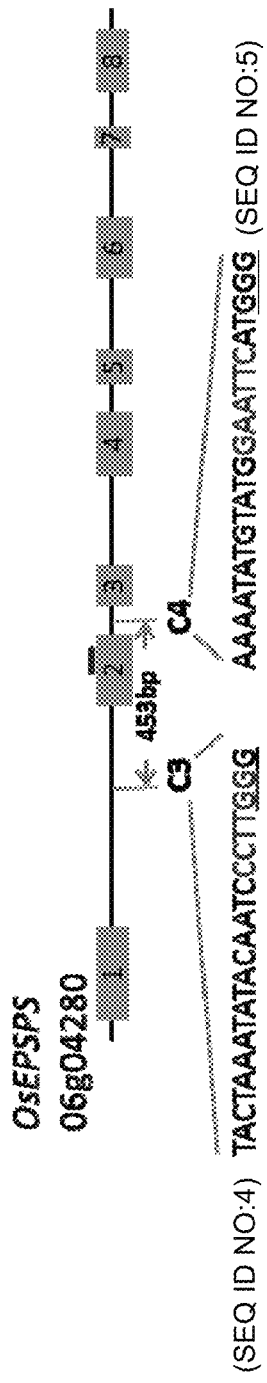
FIG. 1 is a schematic diagram showing the structure of OsEPSPS gene and sequences of two target sites (C3 and C4) for the CRISPR/Cas9 technology. The sequence of TACTAAATATACAATCCCTTGGG is SEQ ID NO: 4 and the sequence of AAAATATGTATGGAATTCATGGG is SEQ ID NO: 5.

Example 1. Selection of OsEPSPS Target Sites of Rice and Construction of a CRISPR Vector I. Selection of an OsEPSPS Target Site The locus number of an OsEPSPS gene is 06g04280, and the OsEPSPS gene is positioned on chromosome No. 6 of rice, contains 8 exons and 7 introns, and encodes 515 amino acids. The conserved region of the OsEPSPS gene is positioned in the second exon, and the target sites selected for construction of knockout vectors are respectively positioned in the first intron and the second intron (FIG. 1). The sequence of the first intron, a second exon containing the conserved region and the second intron of the OsEPSPS gene in a genome of rice is shown in SEQ ID No. 3, wherein position 1-704 of SEQ ID No. 3 is the first intron, position 705-949 is the second exon, and position 950-1030 is the second intron.

One strand of a target double-strand for CRISPR knockout technology has the following structure: 5-Nx-NGG-3, the N in PAM (NGG) represents any one of A, T, C and G, N in Nx represents any one of A, T, C and G, and x is equal to 20. The target sequence of the OsEPSPS gene is as follows, and the underlined is PAM (Protospacer adjacent motif). Target C3 is positioned in the first intron, and target C4 is positioned in the second intron.

(SEQ ID No. 4)
C3: 5'-TACTAAATATACAATCCCTTGGG-3';

(SEQ ID No. 5)
C4: 5'-AAAATATGTATGGAATTCATGGG-3'.

After the rice was transformed by the knockout vector, Cas9 protein cleaved the target sequence region under the mediation of gRNA to form DNA double-strand breaks, the self-damage repair mechanism in the organism was triggered, and mutations (the 'mutation' referred to any mutation, including an insertion mutation, a deletion mutation, a substitution mutation and other forms, and the vast majority of these mutations were gene function inactivation mutations) would be introduced during the process that the cell repairs the gap spontaneously.

The above-mentioned target sequence C3 contains a BsaJI enzyme digestion recognition sequence (sequence in bold italic), and can be cleaved by a BsaJI restriction enzyme; the above-mentioned target sequence C4 contains an EcoRI enzyme digestion recognition sequence (sequence in bold italic), and can be cleaved by an EcoRI restriction enzyme. After the C3 target sequence region was cleaved, if the mutation occurred, the BsaJI enzyme digestion recognition sequence would be destroyed and can not be cleaved by the restriction enzyme BsaJI; if no mutation occurred, the BsaJI enzyme digestion recognition sequence can be cleaved by the restriction enzyme BsaJI. Similarly, after the C4 target sequence region was cleaved, if the mutation occurred, the EcoRI enzyme digestion recognition sequence would be destroyed and can not be cleaved by the restriction enzyme EcoRI; if no mutation occurred, the EcoRI enzyme digestion recognition sequence can be cleaved by the restriction enzyme EcoRI.

II. Construction of Recombinant Vectors

1. The pHUN411 plasmid (the plasmid contains two BsaI restriction enzyme recognition sites) was digested by the restriction enzyme BsaI, and a vector backbone of about 12.5 kb was recovered, and named HUN411.

2. According to C3 and C4 target site sequences designed by step I, primers with cohesive ends (underlined) were synthesized as follows:

```
                                    (SEQ ID NO. 15)
C3-F: 5'-GGCGTACTAAATATACAATCCCTT-3';

(SEQ ID NO. 16)
C3-R: 5'-AAACAAGGGATTGTATATTTAGTA-3'.

(SEQ ID NO. 17)
C4-F: 5'-GGCGAAAATATGTATGGAATTCAT-3';

(SEQ ID NO 18)
C4-R: 5'-AAACATGAATTCCATACATATTTT-3'.
```

3. C3-F and C3-R as well as C4-F and C4-R were annealed respectively to form double-stranded DNAs with cohesive ends named C3 and C4, which were ligated to a gel recovery product HUN411 in the step 1 to obtain recombinant plasmids pHUN411-C3 and pHUN411-C4.

The structure of the recombinant plasmid pHUN411-C3 was described as follows: the recombinant plasmid was obtained by substituting the small fragment (about 1.2 kb) between two restriction enzymes BsaI of the pHUN411 vector with a DNA fragment corresponds to position 1-20 of SEQ ID No. 4, and the plasmid can be used for transcribing a guide RNA containing SEQ ID No. 4 and expressing a Cas9 protein.

The structure of the recombinant plasmid pHUN411-C4 was described as follows: the recombinant plasmid was obtained by substituting the small fragment (about 1.2 kb) between two restriction enzymes BsaI of the pHUN411 vector with a DNA fragment corresponds to position 1-20 of SEQ ID No. 5, and can be used for transcribing a guide RNA containing SEQ ID No. 5 and expressing a Cas9 protein.

Example 2. Transformation of Rice Protoplasts and Detection of Activity of Recombinant Vectors in Protoplasts The recombinant plasmids pHUN411-C3 and pHUN411-C4 constructed in Example 1 were respectively delivered into the protoplasts of rice (*Oryza sativa L. japonica.* cv. Nipponbare) through a PEG-mediated approach. The genomic DNAs of the protoplasts were extracted, and OsEPSPS gene containing target sites C3 and C4 was amplified by PCR using specific primers. Then PCR amplification products containing the target sites C3 and C4 were respectively digested with restriction enzymes BsaJI and EcoRI (if some bands of the PCR amplification products can not be cleaved, it indicates that the target sites designed in the Example 1 are effective). The PCR amplification products which could not be digested by the restriction enzymes were subjected to gel recovery, and inserted to a pEASY-Blunt vector (TransGen Biotech Co., Ltd., catalogue number: CB101), and individual colonies were selected for sequencing.

The primers for respectively amplifying the gene containing the target sites C3 and C4 had sequences as follows:

```
Upstream primer OsEC3-F:
                                    (SEQ ID NO. 19)
5'-CTAGGAATTATCTCTCAAGTCAATC-3';

Downstream primer OsEC3-R:
                                    (SEQ ID NO. 20)
5'-CTCACTGTTCAGCAAGTTGTCC-3'.

Upstream primer OsEC4-F:
                                    (SEQ ID NO. 21)
5'-TTCTTAATAGCTTTGATCGCG-3';

Downstream primers OsEC4-R:
                                    (SEQ ID NO 22)
5'-TAACCTTGCCACCAGGAAGTC-3'.
```

During the experiment, an undigested PCR product control of wild type rice (*Oryza sativa L. japonica.* cv. Nipponbare) and a wild type PCR product control digested by BsaJI or EcoRI were set. The experiment was repeated three times.

Figures 2A, 2B:
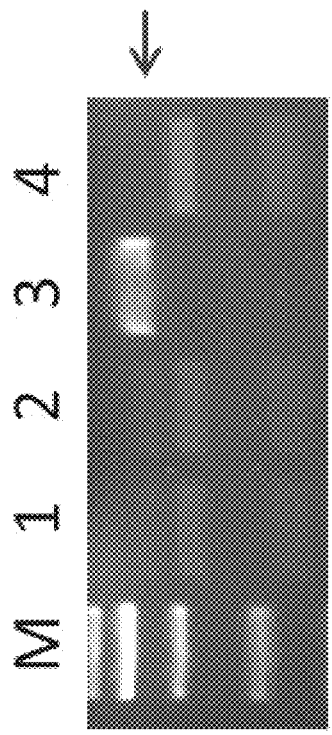
FIGS. 2A-2D show the detection of activity of C3 and C4 targeting OsEPSPS in rice protoplasts and corresponding sequencing results.

The enzyme digestion results for detecting the activity of the C3 recombinant vectors in the protoplasts were shown in FIG. 2a, lanes 1 and 2 were transformed protoplasts, which contain PCR bands that could not be cleaved by BsaJI (the size was about 640 bp, as expected), indicating that the target site C3 is effective; lane 3 was an undigested wild type PCR product control; lane 4 was a digested wild type PCR product control that could be completely digested by BsaJI. The sequencing results (FIG. 2b) indicated that an insertion or a deletion of a small number of nucleotides occurred at the target sites, and confirmed that the recombinant vector pHUN411-C3 performed site-directed gene editing at the target site C3.

Figures 2C, 2D:
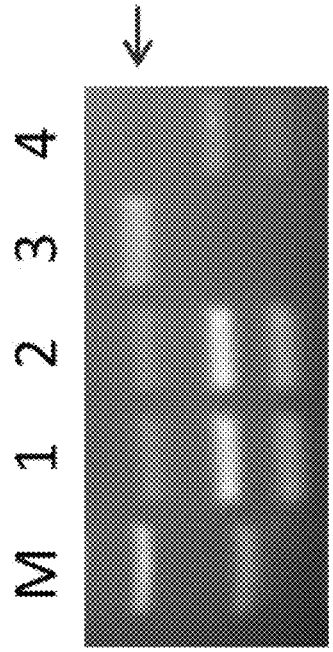

The enzyme digestion results for detecting the activity of the C4 recombinant vectors in the protoplasts through were shown in FIG. 2 c, lanes 1 and 2 were transformed protoplasts, which contain PCR bands that could not be cleaved by EcoRI (the size was about 730 bp, as expected), indicating that the target site C4 is effective; lane 3 was an undigested wild type PCR product control; lane 4 was a digested wild type PCR product control that could be completely cleaved by EcoRI. The sequencing results (FIG. 2b) indicated that an insertion or a deletion of a small number of nucleotides occurred at the target sites, and confirmed that the recombinant vector pHUN411-C4 performed site-directed gene editing at the target site C4.

Example 3. Construction of Donor Vector

This example was intended to construct a donor vector containing a mutation target sequence so that the donor vector can be used together with CRISPR/Cas9 nucleases to achieve substituting threonine (T) at position 8 of the conserved region polypeptide (the coding gene of the conserved region polypeptide is SEQ ID No. 1 in the sequence listing) as shown in SEQ ID No. 2 in rice endogenous EPSPS protein with isoleucine (I), and substituting proline (P) at position 12 with serine (S). Namely, the sequence of the mutated conserved region polypeptide was SEQ ID No. 7 in the sequence listing, and the mutation was called TIPS mutation for short hereinafter. The specific construction method of the donor vector was as follows:

the genomic DNA of the wild type rice (*Oryza sativa L. japonica*. cv. Nipponbare) was used as a template, and a primer pair OsEPSPS-DF/OsEPSPS-DR was used for PCR amplification. Amplification product was subjected to electrophoresis detection. A target band of 1.2 Kb was obtained, and the PCR product was purified and ligated to pEASY-Blunt vector (TransGen Biotech Co., Ltd., catalogue number: CB101). A clone containing the EPSPS fragment was obtained after PCR verification, and the plasmid was extracted. The sequencing results indicated that the plasmid as obtained contains a DNA fragment shown in SEQ ID No. 8 inserted into the T-Blunt vector, which was named TB-EPSPS-D. Positions 12 to 1041 of SEQ ID No. 8 were completely identical to SEQ ID No. 3.

```
                                        (SEQ ID NO. 23)
OsEPSPS-DF: 3'5'-CCCTCTCCGAGGTGAGACG- (position
1-19 of SEQ ID No. 8);
                                        (SEQ ID NO. 22)
OsEPSPS-DR: 5'-TAACCTTGCCACCAGGAAGTC-3' (a reverse
complementary sequence of position 1179-1199 of
SEQ ID No. 8).
```

The plasmid TB-EPSPS-D was used as a template, and amplified with the primers OsEPSPS-TIPSF/OsEPSPS-TIPSR (to facilitate the later detection, PvuI restriction enzyme digestion sites were designed by synonymous mutation in both primers). PCR product was treated by DpnI, and transformed into *E. coli*. A clone was selected and sent for sequencing. After sequencing, the recombinant plasmid obtained be inserting a DNA fragment shown in SEQ ID No. 6 to the T-Blunt vector was named pEPSPS-donor. The difference between the SEQ ID No. 6 and SEQ ID No. 8 was only a mutation site introduced into the OsEPSPS-TIPSF/OsEPSPS-TIPSR primer, and the mutated amino acid sequence in the conserved region was shown in SEQ ID No. 7 in the sequence listing.

Figure 3B:
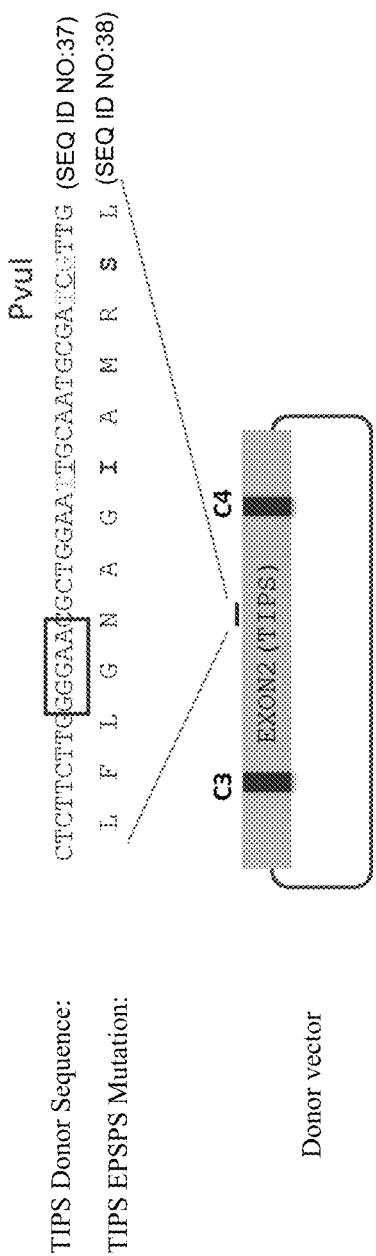
Figure 4A:
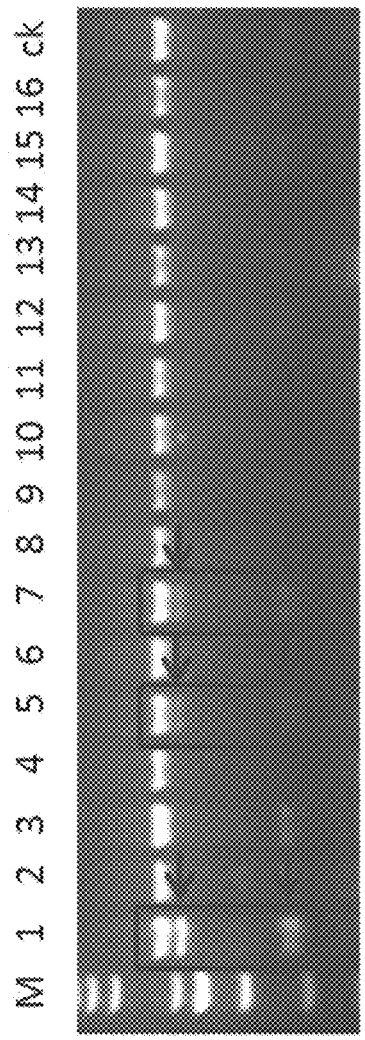

A schematic diagram showing the structure of PEPSPS-donor was shown in FIG. 3.

```
                                                      (SEQ ID NO. 24)
OsEPSPS - TIPSF: 5 '- GAACGCTGGAATTGCAATGCGATCGTTGACAGCAGCCGTGAC - 3';

(SEQ ID NO. 25)
OsEPSPS - TIPSR: 5 '- TGCTGTCAAcGATCGCATTGCAATTCCAGCGTTCCCCAAG - 3'.
```

Mutation nucleotides were shown in frames, and enzyme digestion sites PvuI resulted from mutations was shown in bold.

Example 4. Transformation of Rice and Detection of TIPS EPSPS Mutants

The recombinant plasmids pHUN411-C3 and pHUN411-C4 constructed in Example 1 and the recombinant plasmid pEPSPS-donor constructed in Example 3 were co-introduced into rice (*Oryza sativa L. japonica*. cv. Nipponbare) through a gene gun transformation method at the same time. The callus of the rice (*Oryza sativa L. japonica*. cv. Nipponbare) was used as transformation recipient; the molar ratio of the recombinant plasmids pHUN411-C3 to pHUN411-C4 to pEPSPS-donor during co-transformation was 1:1:2. Complete plants (namely, T0 generation) were regenerated by tissue culture after transformation.

The genomic DNA of T0-generation transgenic plant was extracted, and the specific primers OsEF1 and OsER containing the target sites C3 and C4 and a TIPS mutation site were used for PCR amplification on the genomic DNA.

```
                                        (SEQ ID NO. 26)
OsEF1: 5'-CAACAGGATCCTCCTCCTCTC-3' (positioned at
30 bp upstream SEQ ID No. 8/6 in a rice genome);
                                        (SEQ ID NO. 22)
OsER: 5'-TAACCTTGCCACCAGGAAGTC-3' (a sequence
reverse complementary to position 1179 to 1199 of
SEQ ID No. 6).
```

PCR product was digested with a single enzyme PvuI, and the enzyme digestion result was shown in FIG. 4*a*. After PCR and enzyme digestion detection, three lines of plants with mutations at the TIPS site were obtained, such as T0-1, T0-5, T0-7 (respectively corresponding to lanes 1, 5 and 7 in FIG. 4*a*, which also contain target bands (with the size of about 950 bp and 270 bp) from digestion of PvuI in addition to a PCR product band (with the size of about 1.2 kb)), the remaining numbered plants (respectively corresponding to lanes 2, 3, 4, 6, 8, 9, 10, 11, 12, 13, 14, 15 and 16 in FIG. 4) belonged to the wild type.

Furthermore, the sequencing results of mutants were shown in FIG. 4*b*. The three lines (T0-1, T0-5, and T0-7) contain target nucleotide mutations at the designed target sites, and the insertion and deletion of a small number of nucleotides were generated at the target sites C3 and C4 at the same time. Because C3 and C4 were positioned in the introns, the open reading frame of OsEPSPS gene was not affected by the deletion and insertion of a small number of nucleotides. An the protein generated from translation was affected by the target nucleotide mutations, indicating that mutants containing mutations at TIPS EPSPS site were successfully obtained.

Example 5. Verification of Glyphosate Resistance of TIPS EPSPS Site Mutants

The three TIPS EPSPS site mutation lines (T0-1, T0-5 and T0-7) obtained from Example 4 and wild type rice (*Oryza sativa L. japonica*. cv. Nipponbare) plants were placed into an N6 culture medium containing 1 mg/L glyphosate, and cultured under the routine culture conditions. The resistance results were recorded after 10 days. Verification was carried out in more than 3 plants for each TIPS EPSPS site mutation line.

Figure 5:
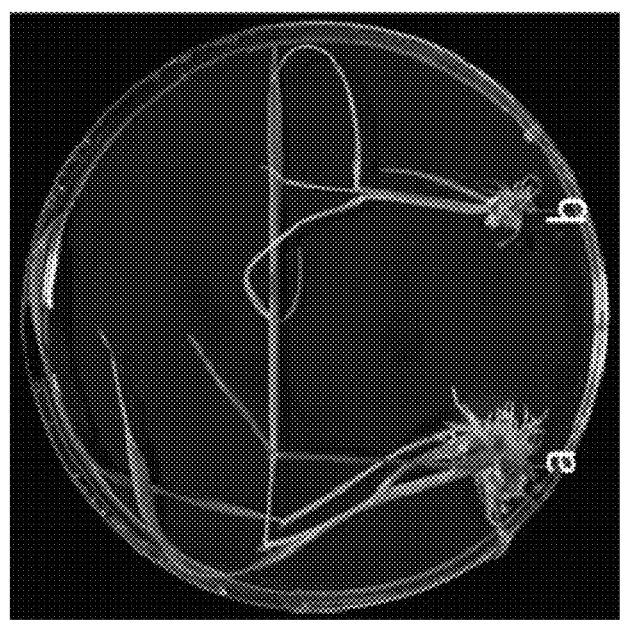
FIG. 5 shows the growth of a rice plant in N6 culture medium containing 1 mg/L glyphosate. After cultivation for 10 days, a) represents a mutant T0-1 obtained by making TIPS site-directed mutation in OsEPSPS gene; b) is a control of wild type rice (*Oryza sativa L. japonica.* cv. Nipponbare).

The results showed that the wild type rice (*Oryza sativa L. japonica*. cv. Nipponbare) plants had become chlorotic and wilting to die, and all the TIPS EPSPS site mutation plants survived normally (leaves thereof were green). FIG. 5a shows TIPS EPSPS site mutated T0-1, and FIG. 5b shows a wild type rice (*Oryza sativa L. japonica*. cv. Nipponbare) control plant.

Example 6. Intron-Mediated Site-Specific Gene Replacement in *Arabidopsis thaliana*

Generation of precise modifications of genome such as point mutations and gene replacements have been of great value for functional genomic studies in *Arabidopsis thaliana*, which is a model plant of dicotyledon. We report here an intron-mediated site-specific gene replacement approach via the non-homologous end joining (NHEJ) pathway using the CRISPR/Cas9 system in *Arabidopsis thaliana*.

A point mutation (G1654-A) in Atsnc1 (At4g16890) leading to the Glu552-to-Lys-552 substitution, was identified previously that constitutively expresses pathogenesis-related (PR) genes and could confer the plant with resistance against both *Pseudomonas syringae* pv *maculicola* ES4326 and *Peronospora parasitica* Noco2. Hence we set out to obtain an amino acid substitution of the endogenous Atsnc1 gene. The genomic sequence of Atsnc1 is SEQ ID No. 9.

The point mutation occurs in Exon 3 of Atsnc1 and the coding sequence of Exon 3 is SEQ ID No. 10. To replace the endogenous exon 3 with a new exon containing the point mutation (G1654-A) (SEQ ID No. 11), we designed dual sgRNAs targeting introns 2 and 3 of Atsnc1, respectively. The sgRNA targeting the intron 2 of Atsnc1 is SEQ ID No. 12 (S1) and the sgRNA targeting the intron 3 of Atsnc1 is the SEQ ID No. 13 (S2).

We integrated S1 sgRNA (driven by the AtU626 promoter), S2 sgRNA (driven by the AtU629 promoter) and donor sequence containing one nucleotide substitution (G1654-A) into the pHEE401 vector carrying hygromycin B phosphotransferase (hpt) and Cas9 expression cassettes, resulting in the construct pHEE411-S1S2Donor. The donor sequence containing the nucleotide substitution is SEQ ID No. 14.

The final vector pHEE411-S1S2Donor is transformed into *Agrobacterium* strain GV3101 using freeze-thaw method. *Arabidopsis* Col-0 wild-type plants were used for transformation via the floral dip method. The collected seeds were screened on MS plates containing 25 mg/L hygromycin. Genomic DNA was extracted from T1 transgenic plants grown in soil. Fragments surrounding the target sites were amplified by PCR using gene-specific primer and sequenced. Finally the gene replacement plants were obtained.

What is claimed is:

1. A method for substituting a target nucleotide for a desired nucleotide in a target gene of a target plant's genome, comprising the step of introducing the following into a cell or tissue of the target plant via gene gun transformation:
 a first genetic material, a second genetic material and a donor vector: the first genetic material is a circular DNA plasmid, a linear DNA fragment or an RNA transcribed in vitro capable of expressing a first CRISPR/Cas9 nuclease; the second genetic material is a circular DNA plasmid, a linear DNA fragment or an RNA transcribed in vitro capable of expressing a second CRISPR/Cas9 nuclease;
 wherein the first CRISPR/Cas9 nuclease is able to specifically cleave a first target fragment in the genome of the target plant and the donor vector; and wherein the second CRISPR/Cas9 nuclease is able to specifically cleave a second target fragment in the genome of the target plant and the donor vector,
 wherein the donor vector additionally comprises a mutation target sequence released by the cleavage of the donor vector by the first and second CRISPR/Cas9 nucleases; the mutation target sequence contains a DNA fragment sequence corresponding to a sequence in the genome of the target plant from the 5' end of a first target fragment to the 3' end of a second target fragment, which contains the desired nucleotide substitution;
 wherein the first target fragment is positioned in an intron region or a promoter region in the genome of the target plant upstream of the target nucleotide of the target gene in the genome of the target plant;
 wherein the second target fragment is positioned in an intron region or a 3'-UTR region in the genome of the target plant downstream of the target nucleotide of the target gene in the genome of the target plant,
 wherein the target nucleotide is located in an exon of the target gene,
 wherein the first genetic material, the second genetic material, and the donor vector are delivered simultaneously in a molar ratio of 1:1:2.

2. The method according to claim 1, wherein the cell is any cell that can be used as an introduction recipient and can be regenerated into a complete plant by tissue culture; or the tissue is any cell that can be used as an introduction recipient and can be regenerated into a complete plant by tissue culture.

3. The method according to claim 2, wherein said plant is *Arabidopsis*; said target gene is Atsnc1(At4g16890) of SEQ ID NO: 9; said first sequence specific nuclease comprises a sgDNA corresponding to SEQ ID NO: 12; said second sequence specific nuclease comprises a sgDNA corresponding to SEQ ID NO: 13; said mutation target sequence is set forth in SEQ ID NO.14; substitution of the target nucleotide results in the replacement of Exon 3 of Atsnc1 of SEQ ID NO: 10 with SEQ ID NO: 11, and thus conferring on the plant the resistance against *Pseudomonas syringae* pv *maculicola* ES4326 and *Peronospora parasitica* Noco2.

4. The method according to claim 1, wherein said target plant is rice or *Arabidopsis*.

5. A method for obtaining a glyphosate-resistant plant, the method comprising:
 substituting threonine (T) at position 8 of the amino acid sequence of a conserved region of endogenous EPSPS protein of a target plant with isoleucine (I), and substituting proline (P) at position 12 with serine (S) to obtain a glyphosate-resistant plant,
 wherein the conserved region of the endogenous EPSPS protein of the target plant comprises the amino acid sequence of SEQ ID NO: 2,
 wherein the substituting step comprises introducing the following into a cell or tissue of the target plant via gene gun transformation:
 a first genetic material, a second genetic material and a donor vector: the first genetic material is a circular DNA plasmid, a linear DNA fragment or an RNA transcribed in vitro capable of expressing a first CRISPR/Cas9 nuclease; the second genetic material is a circular DNA plasmid, a linear DNA fragment or an RNA transcribed in vitro capable of expressing a second CRISPR/Cas9 nuclease;
 wherein the first CRISPR/Cas9 nuclease is able to specifically cleave a first target fragment in the genome of the target plant and the donor vector; and wherein the second CRISPR/Cas9 nuclease is able to specifically cleave a second target fragment in the genome of the target plant and the donor vector,
 wherein the donor vector additionally comprises a mutation target sequence released by the cleavage of the donor vector by the first and second CRISPR/Cas9 nucleases; the mutation target sequence contains a DNA fragment sequence corresponding to a sequence in the genome of the target plant from the 5' end of a first target fragment to the 3' end of a second target fragment, which contains the desired nucleotide substitution;
 wherein the first target fragment is positioned in an intron region or a promoter region in the genome of the target plant upstream of the nucleotide sequence encoding the amino acid sequence of the conserved region of the endogenous EPSPS protein,
 wherein the second target fragment is positioned in an intron region or a 3'-UTR region in the genome of the target plant downstream of a nucleotide sequence encoding the amino acid sequence of the conserved region of the endogenous EPSPS protein,
 wherein the nucleotide substitution is a mutation by which threonine (T) at position 8 of the amino acid sequence of the conserved region of endogenous EPSPS protein of a target plant is substituted with isoleucine (I), and proline (P) at position 12 is substituted with serine (S), and wherein the first genetic material, the second genetic material, and the donor vector are delivered simultaneously in a molar ratio of 1:1:2.

6. The method according to claim 5, wherein
(a) the first target fragment is positioned in an intron region in the genome of the target plant upstream of the first intron region comprising a nucleotide sequence encoding the amino acid sequence of the conserved region of the endogenous EPSPS protein; wherein the nucleotide sequence of the first intron region comprises the nucleotides from position 1 to 704 of SEQ ID NO: 3; wherein both the first sequence specific nuclease and the second sequence specific nuclease are CRISPR/Cas9 nucleases, and wherein the first target fragment is a fragment complying with the formula of 5'-$N_X$-NGG-3' or 5'-CCN-$N_X$-3' within the nucleotide sequence corresponds to position 1-704 of SEQ ID NO: 3; wherein N represents any one of A, G, C, and T; 14≤X≤30 and X is an integer; and wherein $N_X$ represents X consecutive nucleotides; and/or
(b) the second target fragment is positioned in an intron region in the genome of the target plant downstream of the second intron region comprising a nucleotide sequence encoding the amino acid sequence of the conserved region of the endogenous EPSPS protein, wherein the nucleotide sequence of the second intron region comprises the nucleotides from position 950 to 1030 of SEQ ID No. 3, and wherein both the first and second sequence specific nucleases are CRISPR/Cas9 nucleases, and wherein the second target fragment is a fragment comprising a sequence of the formula of 5'-$N_X$-NGG-3' or 5'-CCN-$N_X$-3' within a nucleotide sequence comprised of the nucleotides from position 950 to 1030 of SEQ ID NO: 3,
wherein N represents any one of A, G, C, and T; 14≤X≤30 and X is an integer; and $N_X$ represents X consecutive nucleotides.

7. The method according to claim 6, wherein the nucleotide sequence of the first target fragment is SEQ ID NO: 4; and wherein the nucleotide sequence of the second target fragment is SEQ ID NO: 5.

8. The method according to claim 7, wherein the first genetic material is a recombinant plasmid obtained by substituting the fragment between two restriction enzymes BsaI of the pHUN411 vector with a DNA fragment corresponds to position 1-20 of SEQ ID NO: 4, wherein the second genetic material is a recombinant plasmid obtained by substituting the fragment between two restriction enzymes BsaI of the pHUN411 vector with a DNA fragment corresponds to position 1-20 of SEQ ID NO: 5, or wherein the nucleotide sequence of the mutation target sequence carried by the donor vector is set forth in SEQ ID NO: 6.

9. The method according to claim 5, wherein the cell is any cell that can be used as an introduction recipient and can be regenerated into a complete plant by tissue culture, and wherein the tissue is any tissue that can be used as an introduction recipient and can be regenerated into a complete plant by tissue culture.

\* \* \* \* \*